(12) United States Patent
Pushpangadan et al.

(10) Patent No.: US 7,128,924 B2
(45) Date of Patent: Oct. 31, 2006

(54) SAFE, ECO-FRIENDLY, HEALTH PROTECTIVE HERBAL COLORS AND AROMA USEFUL FOR COSMACEUTICAL APPLICATIONS

(75) Inventors: Palpu Pushpangadan, Uttar Pradesh (IN); Shanta Mehrotra, Uttar Pradesh (IN); Ajay Kumar Singh Rawat, Uttar Pradesh (IN); Sayyada Khatoon, Uttar Pradesh (IN); Raghavan Govindarajan, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/846,270

(22) Filed: May 2, 2001

(65) Prior Publication Data

US 2002/0187115 A1  Dec. 12, 2002

(51) Int. Cl.
*A61K 6/00* (2006.01)
*A61K 7/00* (2006.01)
*A61K 35/12* (2006.01)

(52) U.S. Cl. ............. 424/401; 424/520; 424/742; 424/773

(58) Field of Classification Search ........ 424/461, 424/520, 724, 773
See application file for complete search history.

(56) References Cited

U.S. PATENT DOCUMENTS

| | | | |
|---|---|---|---|
| 4,996,044 A | 2/1991 | Mercado et al. | ............ 424/64 |
| 5,110,593 A * | 5/1992 | Benford | |
| 5,593,662 A | 1/1997 | Deckner et al. | ............ 424/64 |
| 5,665,778 A | 9/1997 | Semeria et al. | ............ 514/613 |
| 5,676,957 A | 10/1997 | Nakamura et al. | ........... 424/401 |
| 5,858,348 A | 1/1999 | Matsuda et al. | .......... 424/78.38 |
| 6,340,485 B1 * | 1/2002 | Coupland et al. | ........... 424/776 |
| 2002/0082279 A1 * | 6/2002 | Schultz | ............ 514/330 |

FOREIGN PATENT DOCUMENTS

| | | | |
|---|---|---|---|
| CN | 1099051 | * | 2/1995 |
| CN | 1113773 | * | 12/1995 |
| WO | 00/62738 | | 10/2000 |

OTHER PUBLICATIONS

"Naphthaquinones of Amebia Nobills", Y.N. Shukla et al., Phytochemistry, vol. 10, pp. 1909-1915, (1971).
"Naturally Occurring Isohexenylnaphthazarin Pigments: A New Class of Drugs" V.P. Papageorgiou, Planta Medica, vol. 38, No. 3 (1980).

* cited by examiner

*Primary Examiner*—Sreeni Padmanabhan
*Assistant Examiner*—Jennifer Kim
(74) *Attorney, Agent, or Firm*—Foley & Lardner LLP

(57) ABSTRACT

The invention relates to a novel safe and eco-friendly health protective and beauty enhancing herbal compositions having various cosmetic applications such as lipsticks, eye shadows, glow-glitters and rouges, said compositions containing colorants from plants of the family Boraginaceae, the invention also provides a method for preparing the said compositions. The invention also relates the use of lipsticks as a medium of aromatherapy.

19 Claims, 24 Drawing Sheets
(24 of 24 Drawing Sheet(s) Filed in Color)

SAFE, ECO-FRIENDLY, HEALTH PROTECTIVE HERBAL COLORS AND AROMA USEFUL FOR COSMACEUTICAL APPLICATIONS

FIELD OF THE INVENTION

The present invention relates to a safe, eco-friendly, health protective and cosmetic composition useful as lipstick and for other cosmaceutical applications like eye-shadows, skin creams, glow-glitters and rouges.

BACKGROUND AND PRIOR ART

There is worldwide revival of interest in the use of natural colours especially in cosmetics and pharmaceuticals as the synthetic colours are likely to cause many side effects. Keeping this in view the present invention is undertaken to develop purely natural herbal colorants for cosmetic compositions. One aspect of the invention pertains to the development of a herbal composition useful as Lipstick with mood altering functional attributes including stimulation of creative thoughts on persons who apply the same on lips. Such features of the composition are attributed to the selected blended formulations of Natural colours and essential oils/aroma isolates incorporated.

Lips being the most sensitive part of skin, can effect fast transdermal absorption and also the lips being very close to nose facilitate a continuous inhalation of the slowly vaporizing essential oils/aroma chemicals blended in the composition, thus, providing a double effect on the specific centers of the brain by releasing neurochemicals leading to mood alteration stimulation and change of mental perceptions. The different blends of essential oil/aroma isolates/natural aroma chemical selectively blended in the lipsticks provide anti-depressant, mood enhancing/mood lifting effect and give rise to creative thoughts.

While lipsticks with different colour shades blended with aromatic principles have been developed for women, another range of compositions useful as lipsticks has also been developed for men. These compositions are without colours but provide a moisturizing transparent effect and have mood altering functions and are designed to altered mental perception, functioning similar to the lipstick compositions developed for developed for women. Both the groups of lipstick have some additional health promotive/protective and beautifying attributes by preventing the lips from darkening and providing it with moisturizing effects. These compositions also give attractive luster and texture to the lips. The lipsticks with colour, developed for women, have antibacterial, antifungal and anti-inflammatory effects. With regard to lip beautification topical application lipstick with different shades of colours are well known. Likewise, spraying of aromatic oils or sprays for refreshing is also well known. Many studies have been carried out on the effect of fragrance on mental perception; for example, the nice fragrance has an aesthetic impression and multiple positive effects on our life, they are not only for pleasure and seduction, healing and magic products but also for positive mood creators.

DESCRIPTION OF PRIOR ART

Reference is made to a publication titled "Naphthaquinones of *Arnebia Nobilis*" by Y. N. Shukla et al., Phytochemistry, 1971, Vol. 10, pp. 1909 to 1915, wherein, 4-naphthaquinones designated as A-1, A-2, A-3 and A-4 have been reported. The use of the extract from *Arnbia nobilis* is also reported. Sayyada Khatoon and Shanta Mehrotra in "Naphtha quinones from some Boraginaceous Texa-A Chemical Review" published in Natural Product Sciences, 1996 2(2) pp. 75–85 report a number of naphthaquinones from boraginaceous plants. Varies properties of these compounds have also been reported.

V. P. Papageorgiou, has reported certain lipophilic red pigments obtained from various plants including the genus *Lithospermum, Echium Onosma Anchusa* and *Cynoglossum*, in his publication titled: Naturally occurring Isohexenyl-naphthazirin Pigments: A New Class of Drugs" in Planta Medica, 1980, Vol. 38, No. 3.

U.S. Pat. No. 4,996,044 describes a lipstick formulation consisting of organic high staining dyes, said formulation having creamy, shiny and soft laydown and long wear properties. The formulation does not use any extracts from any plant.

Reference is made to a U.S. Pat. No. 5,593,662 wherein moisturizing lipstick has been described. In this invention, use has been made with a composition of 30–80% lipophilic material, which may have lesser shelf life and may promote microbial growth due to the presence of moisture. They used about 0–35% synthetic colourant which seems to be too high for a cosmetic composition. The synthetic colours mostly exhibit harmful side effects like loss of luster, blackening of skin and may have some carcinogenic effects too as shown in a website (http://www.orst.edu/foodresource/color/colorants/.html).

Another reference is made to U.S. Pat. No. 5,665,778 wherein a ceramide, process for their preparation and their application in cosmetics and in dermato-pharmacy. These compounds are complex mixtures of erythro & threo-diasterioisomers. They synthesize these compounds by a complex and costly process. They have used organic pigments for lipstick and there is no herbal colourants being used.

Reference may be made to a recent PCT application PCT/EP00/02217 of 13 Mar. 2000 wherein the inventors have used Zinc salts, particularly Zinc citrate in lipstick to effect antimicrobial property. The drawback in using Zinc or its salts is that mostly they are emetic and cause conjunctivitis as side effect.

In an International Congress of Essential oils, fragrance and flavours (November 1989) the description of use of aroma has not at all been mentioned in lipstick. The available lipsticks in the international market are used as refreshing beautifying agents only.

U.S. Pat. No. 5,665,778 describes yet another cosmetic formulation consisting of ceramides and other compounds. The composition of this patent is a totally synthetic composition.

U.S. Pat. No. 5,676,957 describes a skin external agent, said agent being an extract of the plant of genes *Euonymus* such as *Euonymus alata*.This extract according to this invention may be formulated with a cosmetically acceptable base.

Reference is made to a U.S. Pat. No. 5,858,348 wherein only a single isolate of essential oil like rose oxide has been used in synthetic lipstick and other cosmetic for refreshing feel. Such a single isolates of essential oil will not serve the desired multiple effects like mood enhancing, sensual pleasure and thought inducing state of mind.

To the knowledge of the applicants, there does not exist any lipstick with herbal colours and functional attributes, the cosmaceuticals like eye shadows and glow glitters, rouges with use of herbal colours, likewise the lipstick without colour with functional attributes for men.

OBJECTS OF THE INVENTION

The main objective of the present invention is to provide safe, eco-friendly, health protective and cosmetic composition containing natural colours and aroma/essential oils useful for various cosmaceutical applications.

Another objective of the present invention is to use the herbal colours in lipsticks.

Another objective of the present invention is to provide transparent cosmetic compositions useful as lipsticks and containing essential oils/aroma isolates.

Still another objective of the present invention is to use the herbal colours in other cosmetic compositions like eye shadows, skin creams, glow glitters and rouges.

Yet, another objective of the present invention is to provide the use of the functional lipstick as a means to camouflage leucodermic skin and particularly lips.

Yet another object of the invention is to provide a method for the production of cosmetic compositions containing herbal colourants and useful in other cosmetic applications.

SUMMARY OF THE INVENTION

The invention provides a safe, eco-friendly, health protective and beautifying herbal composition containing colourants and aroma, and useful for various cosmaceutical applications. The invention also provides a process for the preparation of the herbal cosmetic composition comprising extraction of colourants from natural sources such as plants, and mixing the colourants with aroma and other base material for cosmaceutical applications.

DETAILED DESCRIPTION OF THE INVENTION

This invention relates to an herbal cosmetic composition containing colouring agents for topical or external use. More particularly, the invention provides a novel cosmetic composition, useful especially as lipstick. When used as lipstick, the composition contains herbal colourants for which is then blended with selected blends of essential oils or aroma isolates and the composition is capable of altering the mood and mental perception of the person, who applies it.

A safe ecofriendly, health protective and beautifying herbal cosmetic composition containing herbal colourants together with a cosmetically acceptable amount of one or more additives providing special properties and a cosmetically acceptable base material.

Accordingly the present invention provides a composition comprising additives providing special properties are selected from essential oils/aroma isolates obtained from the group of plant species belonging to genera *Acquillaria, Cinnamomum, Cymbopogon Elettaria, Eucalyptus, Geranium, Jasminum, Ocimum, Pelargonium, Rosa, Rosmarinus, Santalum* and *Vetiveria*.

In one embodiment of the invention, the essential oils/aroma isolates act as mood lifting agents, antidepressant agents, anti stress agents, sensual pleasure providing agents, creative thought inducing agents, anxiety reducing agent, refreshing agent, stimulant, soothing agents, anti oxidants, fixative, fragrants, and antimicrobial.

The applicants have found that the herbal colourants are obtained from various plants of the family Boraginaceae. It is the finding of the applicants that a wide spectrum of colors can be obtained from the said plants by using specific solvents in specific proportions. For instance, petroleum ether and chloroform may successfully be used in different proportions for extraction of the colored matter from the said plants in order to achieve a wide spectrum of colors such as pastel red, purplish red, cerise, ruby red, deep magenta, beet root purple, amarynth, dark purple, dark violet, deep violet, deep blue blackish blue, etc. It is pertinent to note that each of the plants listed above are capable of yielding the above spectrum of colors.

The applicants have found that the herbal colorants obtained from various plants together with the essential oil and conventional additives yield a herbal composition which is suitable for cosmetic applications such as lipsticks. This herbal composition is devoid of toxic effects. The applicants also believe that the essential oils and aroma isolates may have the properties of mood enhancement, sensual pleasure, antidepressant and creative thought inducer. Also, the essential oils and aroma isolates may be used in transparent lipstick as a functional attribute.

The proportion in which the coloring matter/coloring compounds can be mixed with essential oils and additives can be readily determined by a person skilled in the art. However, it is preferred that 0.0005% of coloring matter may be mixed with $10^{-6}$% essential oil, 1% lustering agent such as safflower oil. The base and other matters added may make up 100%.

Herbal lipophilic, safe colours are extracted from the plants belonging to the genus *Arnebia, Bixa, Butea, Carthamus, Hibiscus, Jatropha, Lithospermmum, Macrotomia, Maharanga, Nyctanthes, Onosma, Rhododendron,* and *Tagetes* which are known to be non toxic and free from any strong side effects on human body particularly on topical application. The colours extracted from these plants are bright and lustrous and have pronounced antibacterial and anti-inflammatory activities. For example a good bright colourant—red-andora colour, plate No. 8.4 L of Dictionary of colours (Maerz and Paul, 1950) and after applying on lips, [pomegranate to Vernonia purple (plate 6.3 L–6.5 A of the same dictionary)] provides different functional effects such as mood refreshing, concentration enhancing, CNS relaxant, accelerating working rate and improves capacity to work. It is pertinent to note that each of the plants listed herein is capable of yielding a wide spectrum of colours.

Accordingly, the present invention provides safe, eco-friendly, health protective herbal colours and aroma useful for cosmaceutical applications which comprises safe, eco-friendly, health protective and beautifying herbal colourants and aroma useful for cosmaceutical applications, comprising extraction of organic compounds from natural sources such as plants, the said extracted organic compounds being used as a colourant with aroma in base material for cosmaceutical applications.

An embodiment of present invention is that the safe herbal colourants may be isolated from different plant species belonging to the genera of family Boraginaceae which are non-toxic and may be free from any side effects.

Another embodiment of present invention is that the aroma isolates/essential oils may be selected from group of plants—*Aquillaria, Cinnamomum, Cymbopogon, Elettaria, Eucalyptus, Geranium, Pelargonium, Rosa, Rosamarinus, Santalum* and *Vetiveria*.

In other embodiment, the herbal colourants may be used in lipsticks, eye shadows, glow glitters and rouges.

In still other embodiment the lipstick containing essential oils and combinations of aroma isolates may release neurochemicals in the brain through the receptors in mouth and nose and may have the properties of mood enhancement, sensual pleasure, antidepressant and creative thought inducer.

In yet another embodiment of the invention, the antidepressant property imparted by the essential oils are selected from

| Essential Oils | Preferred Ratio |
| --- | --- |
| 1. *Ocimum* oil: *Jasminum* oil: *Cymbopogon* oil | (1:2:1) |
| 2. *Ocimum* oil: *Mentha* oil: *Rosmarinus* oil | (2:1:1) |
| 3. *Jasminum* oil: *Mentha* oil: *Rosmarinus* oil | (1:1:1) |
| 4. *Cymbopogon* oil: *Ocimum* oil: *Mentha* oil | (1:2:1) |
| 5. *Ocimum* oil: *Cymbopogon* oil1 | (2:1) |
| 6. *Mentha* oil: *Rosmarinus* oil | (1:1) |
| 7 *Ocimum* oil | |
| 8. *Rosmarinus* oil | |

In yet another embodiment of the invention, the creative thought-inducing property is imparted by the essential oils selected from

| Essential oil | Preferred ratio |
| --- | --- |
| 1. *Santalum* oil | |
| 2. *Santalum* oil: *Rosa* oil | (1:2) |

In yet another embodiment of the invention, the anti-stress property is imparted by the essential oils selected from

| Essential oil | Preferred ratio |
| --- | --- |
| 1. *Santalum* oil: *Lavandula* oil | (2:1) |
| 2. *Lavandula* oil: *Eucalyptus* oil: *Rosa* oil | (1:1:1) |
| 3. *Eucalyptus* oil: *Rosa* oil | (1:2) |
| 4. *Aquillaria* oil: *Elettaria* oil: *Rosmarinus* oil | (1:1:1) |
| 5. *Jasminum* oil | |
| 6 *Santalum* oil | |
| 7. *Lavandula* oil | |

In yet another embodiment of the invention, the refreshing property is imparted by the essential oils selected from

| Essential oil | Preferred ratio |
| --- | --- |
| 1. *Santalum* oil: *Rosa* oil: *Rosmarinus* oil | (1:1:1) |
| 2. *Santalum* oil: *Pelargonium* oil | (1:2) |
| 3 *Jasminum* oil: *Lavandula* oil | (1:2) |
| 4 *Lavandula* oil | |
| 5 *Santalum* oil : *Rosa* oil | |
| 6 Santulam oil | |

In yet another embodiment of the invention, the sensual feeling property is imparted by the essential oils selected from

| Essential oil | Preferred ratio |
| --- | --- |
| 1. *Jasminum* oil: *Lavandula* oil: *Pelargonium* oil | (1:2) |
| 2. *Ocimum* oil: *Jasminum* oil: Cymbopogon oil | (1:2:1) |
| 3. *Jasminum* oil | |
| 4. *Jasminum* oil: *Lavandula* oil | (2:1) |

In yet another embodiment of the invention, the mood lifting property is imparted by the essential oils selected from

| Essential oil | Preferred ratio |
| --- | --- |
| 1. *Jasminum* oil: *Rosa* oil: *Pelargonium* oil | (1:2) |
| 2. *Rosmarinus* oil | (1:2) |
| 3. *Cymbopogan* oil: *Rosa* oil | (2:1) |
| 4. *Rosa* oil | |
| 5. *Jasminum* oil: *Rosa* oil | |

In yet another embodiment of the invention, the anxiety reducing property is imparted by the essential oils selected from

| Essential oil | Preferred ratio |
| --- | --- |
| 1 *Rosa* oil: *Cinnamomum* oil | (1:2) |

Still another embodiment of the invention is that the essential oils and aroma isolates are used in transparent lipstick as a functional attribute.

Still another embodiment of the invention relates to the composition wherein, tocopherol is used as an antioxidant, which also functions as fixative, and may be present in traces to ppm.

An embodiment is that the process for extraction of organic compounds from natural sources such as plants which comprises drying of plant parts, powdering by known means, the said dried powder being used to extract herbal colourants, optionally treating the said colours with acids or bases taken in different proportions, to produce various shades.

Yet another embodiment, the plant parts may be root, stem, leaf, and the quantum of essential oils used in preparing compositions varies based on the part from which the oil is extracted.

Still another embodiment of the present invention is that the plant parts may be dried at a temperature in the range of 30–45° C., in shade.

An another embodiment the dried plant parts may be powdered to particles of the size in the range of 30–60 mesh.

Further embodiment, the herbal red colourants may be extracted from the plants of the genera *Arnebia, Bixa, Butea, Carthamus, Hibiscus, Jatropha, Lithospermum, Macrotomia, Maharanga, Nyctanthes, Onosma, Rhododendron*, and *Tagetes*. The plants or their parts are put in a Soxhlet apparatus at a temperature of 20–80° C. The solvents selected for the extraction may be non-polar—hexane, petroleum ether, toluene and cyclohexane, wherein the polar solvents are selected from chloroform, acetone, ethyl alcohol and methyl alcohol. The non-polar and polar solvents may be recovered at reduced pressure of 50–100 psi and a temperature of 40–80° C. The herbal colourants are obtained after the recovery of the solvents. The concentrates result colours of various shades such as purplish red, cerise, ruby red, beetroot purple, dark violet, deep blue, and blackish blue colours which are herbal in nature as no trace of organic solvent remains in the final concentrate.

Further, the present invention provides a process for preparation of herbal colourants, which comprises the steps of drying the plant material, powdering the same and percolating it with ethyl or methyl alcohol at a temperature of 20–48° C. The alcohol soluble matter is concentrated at reduced pressure of 50–100 psi and a low temperature of 40–60° C. The concentrate is eluted with silica gel column chromatography using non-polar solvents like—petroleum ether, hexane, cyclohexane, toluene and a mixture of non-polar and polar solvents. The polar solvents used may be like chloroform, acetone, ethylacetate and methanol. The ratio of the non-polar and polar solvents may be 20:1 to 4:1.The concentration of the column fractions may be made at a range of reduced pressure of 80–100 psi and a temperature of 30–60° C. The colours of the concentrate may be pastel red, pale red, purplish red, rose red, cerise, ruby red, deep magenta, beetroot purple, amaranth, dark purple, dark violet, deep violet, deep blue and blackish blue.1

In still another embodiment the herbal colourants may be antimicrobial, anti-inflammatory and may be used in leucoderma, more particularly of lips.

The embodiment of the present invention the herbal colourants may be the mixture of naphthazarins and may be cyclic unsaturated diketones in which double bonds and keto group may be conjugated.

The another embodiment of present invention the herbal colourants may be changed in different shades with organic and inorganic acids. The intensity of colours may be increased with organic acids and may be decreased with inorganic acids. The range of the concentration of the acids may be 0.1–10%.

Still another embodiment of the invention that the herbal colours may be changed with organic and inorganic bases.

Another embodiment of the present invention the base concentration may be in the range of 0.1 to 20%.

Yet another embodiment the herbal colour may be lipophilic and hydrophilic properties may be very minimum.

Still another embodiment the herbal colours may be soluble in organic solvents like—hexane, petroleum ether, benzene, diethyl ether, ethylacetate, chloroform, acetone and alcohol in the range of 30–100%.

In an embodiment, the pH of the extracted herbal colours may be 5–6.

The present invention is aimed to prepare safe, eco-friendly, health protective herbal colours and aroma useful for cosmaceutical applications which comprises extraction of organic compounds from natural sources, the said extracted organic compounds being used as a colourant with aroma in base material for cosmaceutical applications.

The safe herbal colourants may be isolated from different plant species belonging to the genera of the family Boraginaceae which are non-toxic and may be free from any side effects.

The present invention is that the aroma isolates/essential oils may be selected from group of plants—*Aquillaria, Cinnamomum, Cymbopogon, Elettaria, Eucalyptus, Geranium, Pelargonium, Rosa, Rosamarinus, Santalum* and *Vetiveria*. The herbal colourants may be used in lipsticks, eye shadows, glow glitters and rouges.

The lipstick containing essential oils and combinations of aroma isolates may release neurochemicals in the brain through the receptors in mouth and nose and may have the properties of mood enhancement, sensual pleasure, antidepressant and creative thought inducer.

The invention is that the essential oils and aroma isolates may be used in transparent lipstick as a functional attribute.

Another aspect of the invention relates to a process for extraction of organic colourants from the plants, said process comprising obtaining the plant parts, extracting with organic solvents, removing the solvents by conventional methods, concentrating the extract under reduced pressure and optionally treating with acids or bases to produce various shades.

Yet another aspect of the invention relates to a process for the extraction of organic colourants, said process comprising the steps of:
a) drying the plant parts,
b) powdering the dried plant parts,
c) subjecting the dry powder obtained in step (b) to Soxhlet extraction at a temperature in the range of 40–80° C. or cold percolation with organic solvents at a temperature ranging between 20 to 45° C.,
d) concentrating the mixture of step (c) by conventional methods at reduced pressure in the range of 50–100 psi and at a temperature not exceeding 50° C.,
e) mixing the concentrate of step (d) with silica gel in the ratio 1:3 to 2:7 to obtain a slurry,
f) eluting the slurry with organic solvents resulting in various fractions,
g) concentrating the fractions at a pressure in the range of 50–100 psi resulting in herbal colourants, optionally treating the said colours with acids or bases to produce various shades, and
h) obtaining various colours from by treating the said fractions with acids or bases to produce colourants of various shades.

One more aspect of the invention relates yet another process of extraction of herbal colourants from plants of the family Boraginaceae, which comprises; percolating powdered plant parts with alcohol at room temperature resulting in alcohol soluble herbal material, the said herbal material being concentrated by known means at pressures in the range of 50–100 psi and at a temperature in the range of 40–60° C., the said concentrate being made into a slurry with silica gel in a ratio in the range of 1:3 to 2:7, the said slurry being eluted by known means with organic solvents resulting in fractions, the said fractions further being concentrated by known methods at a pressure in the range of 50–100 PSI resulting in herbal colorants, optionally treating the said colours with acids or bases to produce various shades.

The herbal colours may be extracted from any of the three parts of the plants; namely root, stem or leaves or by taking all of them. These parts may then dried by any conventional means which may include heat treatment at a temperature between 30–45° C. Alternatively the drying process may be effected in shade though the time for drying may be rather too long. The dried plant material may then be powdered and sieved through mesh to get a powder of particles of a suitable size preferably in the range of 30–60 mesh.

The dried powder may then be extracted by using Soxhlet apparatus at a temperature range of 40–80° C.

The dried powdered plant material may also be extracted by cold percolation at a temperature range of 20–45° C.

The extraction may be carried out with the non-polar and mixtures of non-polar and polar solvents selected for the extraction. Non-polar solvents may be selected from hexane, petroleum ether, toluene and cyclohexane whereas the polar solvents may be selected from chloroform, acetone, ethyl alcohol and methyl alcohol. The herbal colours may be obtained by concentrating the extracts at reduced pressure of 50–100 psi and a temperature at range of 40–60° C. This process of concentration may result in purplish red, cerise, ruby red, beet root purple, dark violet, deep blue, and blackish blue colours which are herbal in nature as no trace of organic solvent remains in the final concentrate.

In another process, the dried, powdered plant material may be percolated with ethyl or methyl alcohol at a temperature of 20–48° C. The alcohol soluble matter may be concentrated at reduced pressure of 50–100 psi and a low temperature of 40–60° C. Thus, the said concentrate may be eluted with silica gel column chromatography by using non-polar solvents like—petroleum ether, hexane, cyclohexane, toluene and mixture of said non-polar and polar solvents. The polar solvents may be used like—chloroform, acetone, ethylacetate & methanol. The ratio of the non-polar and polar solvents may be 20:1 to 4:1.The concentration of the column fractions may be made at a range of reduced pressure of 80–100 psi and a temperature of 30–60° C. The colours of the concentrate may be pastel red, pale red, purplish red, rose red, cerise, ruby red, deep magenta, beet root purple, amaranth, dark purple, dark violet, deep violet, deep blue and blackish blue.

These novel colours may be used with or without the aroma isolate/essential oils. Proper mixture of aroma isolates/essential oils may result in such desirable properties of mood enhancement, sensual pleasure, antidepressant and creative thoughts inducer To get these desired properties in cosmetics like lipsticks the herbal colours may be mixed with selected mixture of aroma and applied to the base material. These herbal colours may be used in other applications like eye shadow, glow glitters, rouges and skin conditioning agent.

These colours may be the mixture of naphthazarins and may be cyclic unsaturated diketones in which double bonds and keto group may be conjugated. These herbal colours may be changed to different shades by treating it with organic and inorganic acids. The intensity of these colours may be increased with organic acids and may be decreased with inorganic acids. The range of the concentration of the acids may be 0.1–10%. The colour of the herbal colourants may be changed from red to blue with organic and inorganic bases. The range of the concentration of the bases may be 0.1–20%.

These herbal colours may have excellent lipophilic properties and very minimum hydrophilic properties. These colours may be soluble in organic solvents like—hexane, petroleum ether, benzene, diethyl ether, ethylacetate, chloroform, acetone and alcohol in the range of 30–100%. The pH of the extracted colours may be within the range of 5–6.All these characteristics of the herbal colours are very desirable for use in cosmaceutical applications. The process of the present invention can obtain various colours such as described in the tables 3 to 6.

Some of the critical parameters, which are responsible for the generation of various colourants, are as under:
a) composition of the solvent used for running the column chromatography.
b) the ratio of the polar to non-polar solvent is also a critical parameter for the production of the different colours.
c) the temperature of the Rotavapours used in the process of the concentration of the extract is also a critical parameter.
d) the temperature of the hot air oven at which the lipstick formulation is made is also a critical parameter.
e) treating the said colours with specific concentration of acids or bases to produce various shades.

Novel Features of the Invention:
1. Extraction of the herbal colours from plant materials which are non-toxic and highly lipophilic.
2. A novelty of the present invention lies in application of herbal colours in cosmaceutical preparations like lipsticks, eye shadow, glow glitters and rouges.
3. Ability to tailor the shade of the basic herbal colours by a simple treatment of the produce with organic or inorganic acids or bases.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Thus, the process of the invention can be used to achieve different colourants. Some of the colourants obtained are shown in the accompanying drawings. In the accompanying drawings.

BRIEF DESCRIPTION OF THE TABLES

Figure 1:
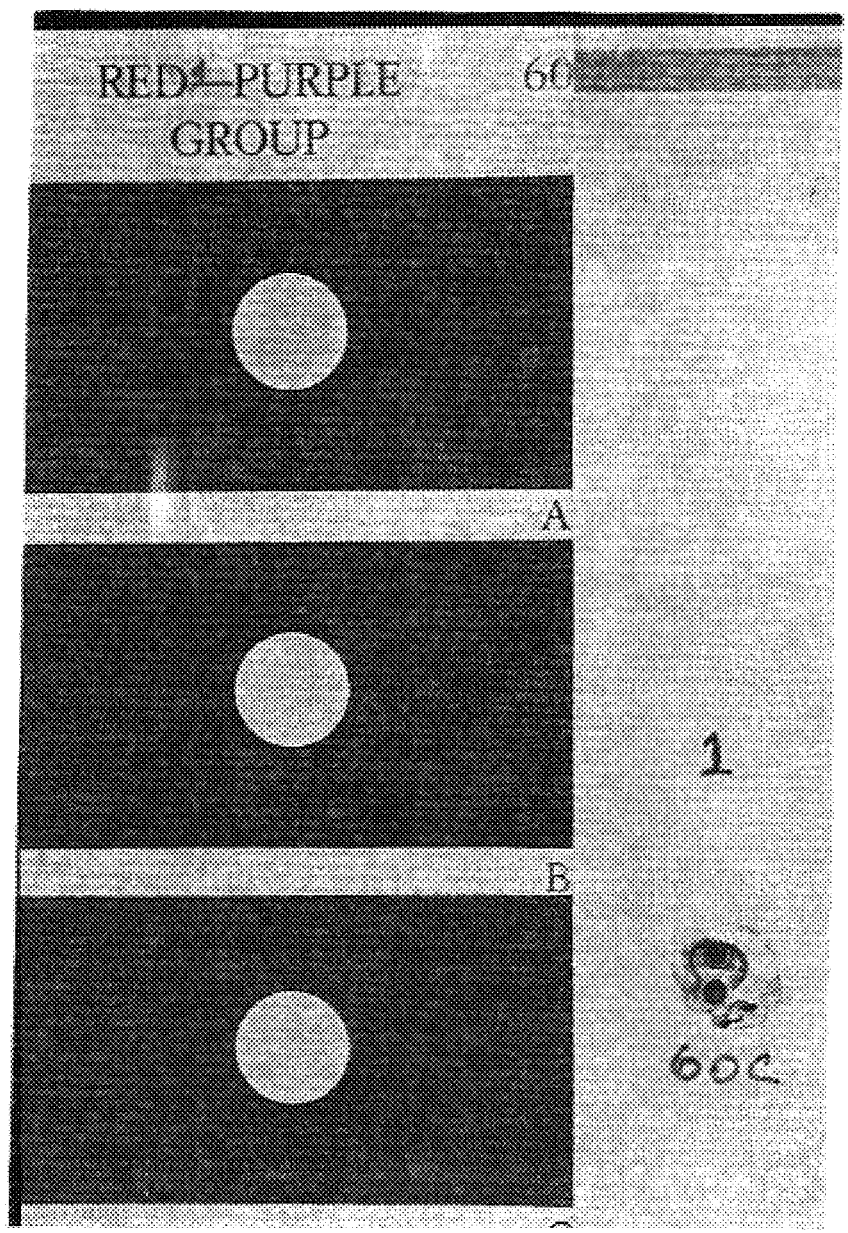
FIG. 1 represents colourant of red-purple group (60C).
Figure 2:
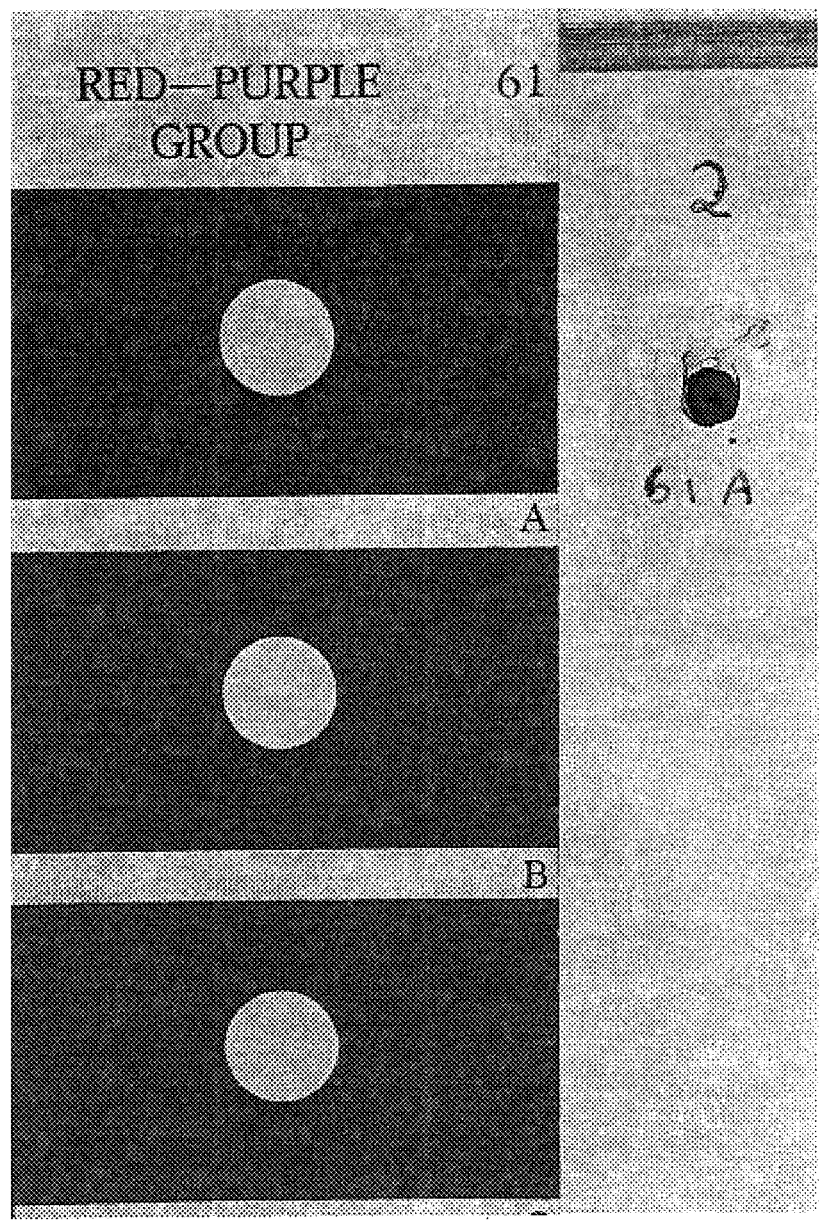
FIG. 2 represents colourant of red-purple group (61A).
Figure 3:
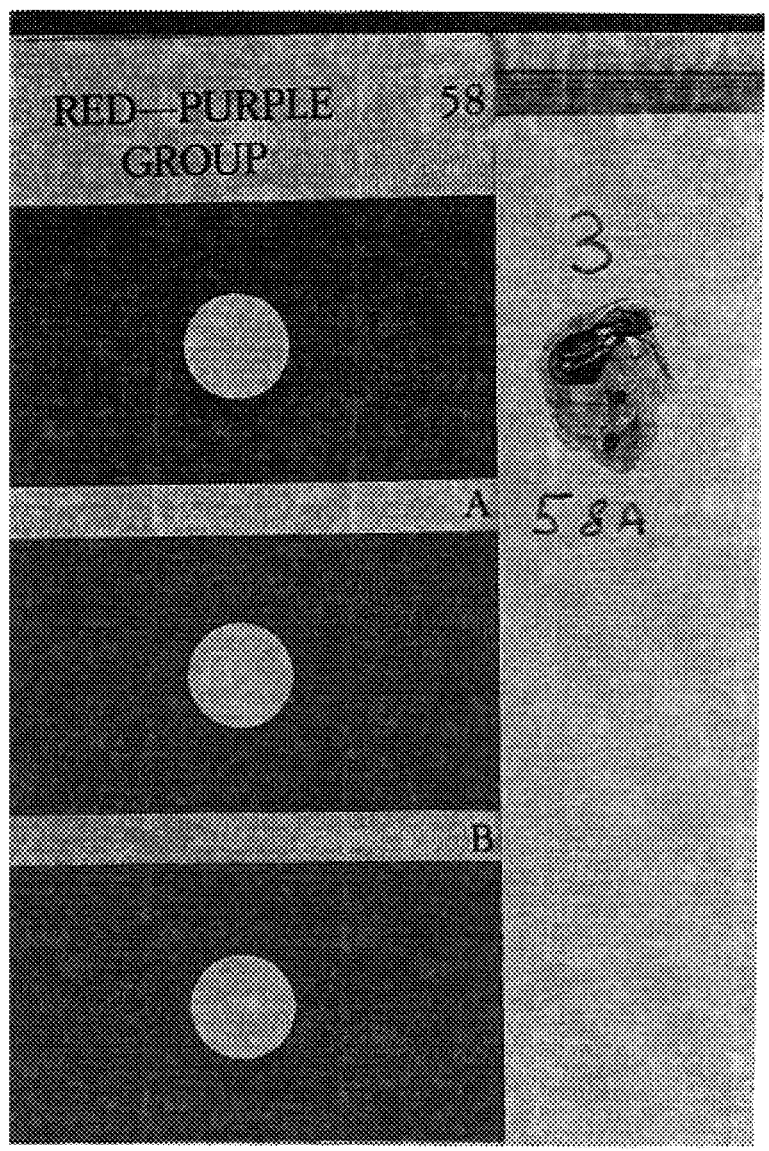
FIG. 3 represents colourant of red-purple group (58A).
Figure 4:
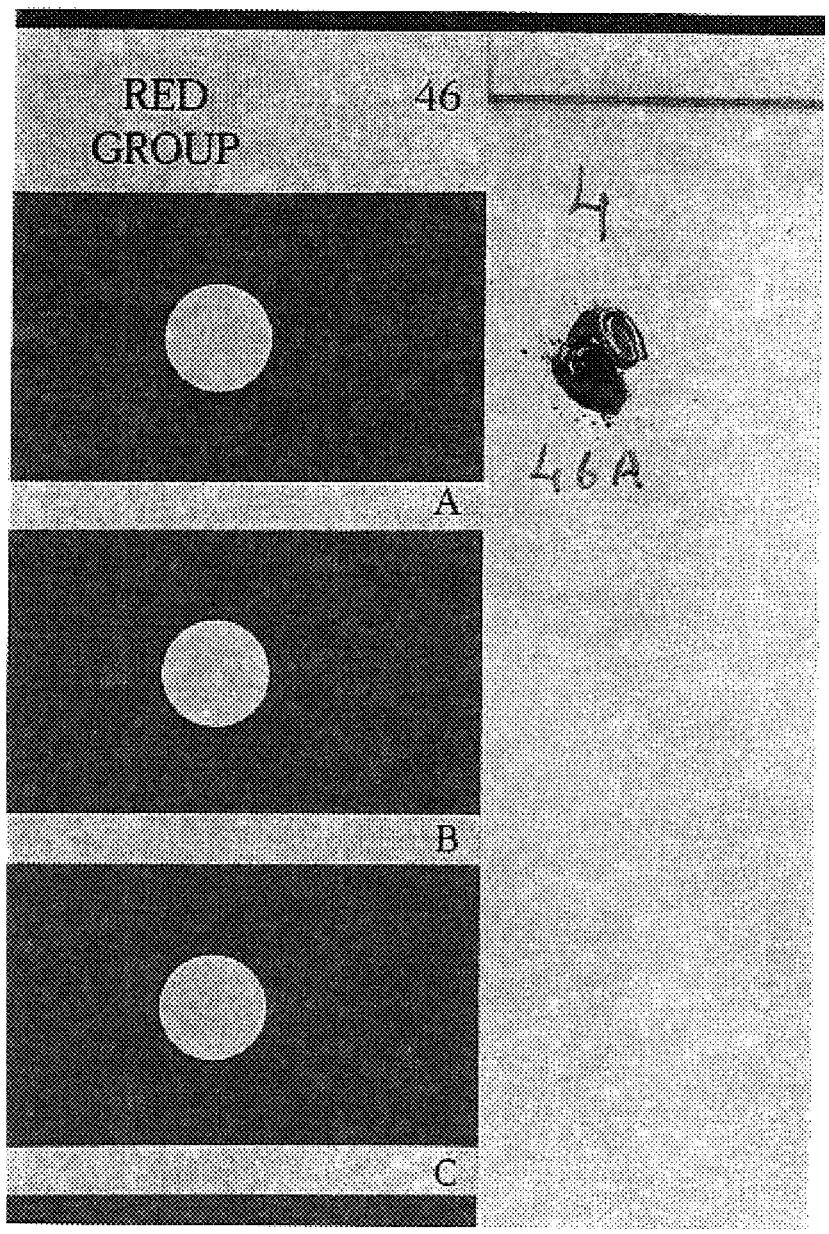
FIG. 4 represents colourant of red-purple group (46A).
Figure 5:
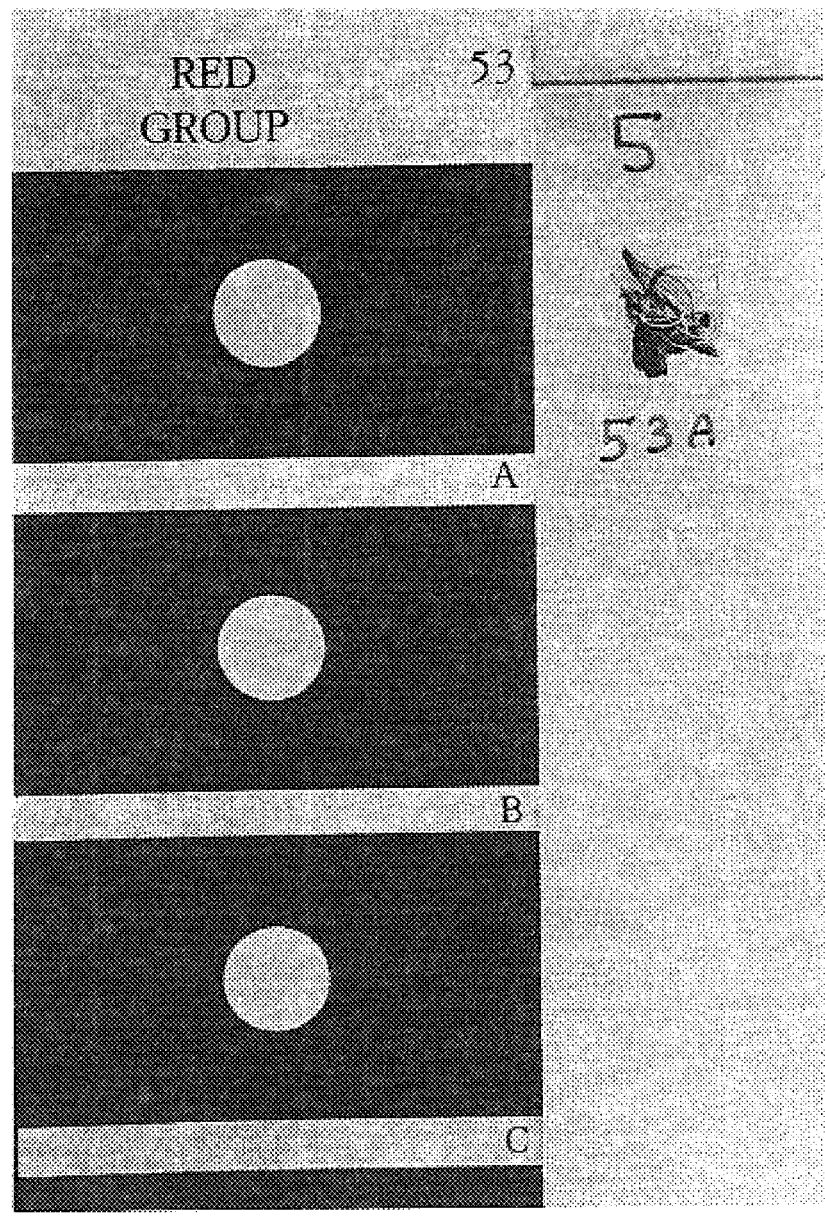
FIG. 5 represents colourant of red-purple group (53A).
Figure 6:
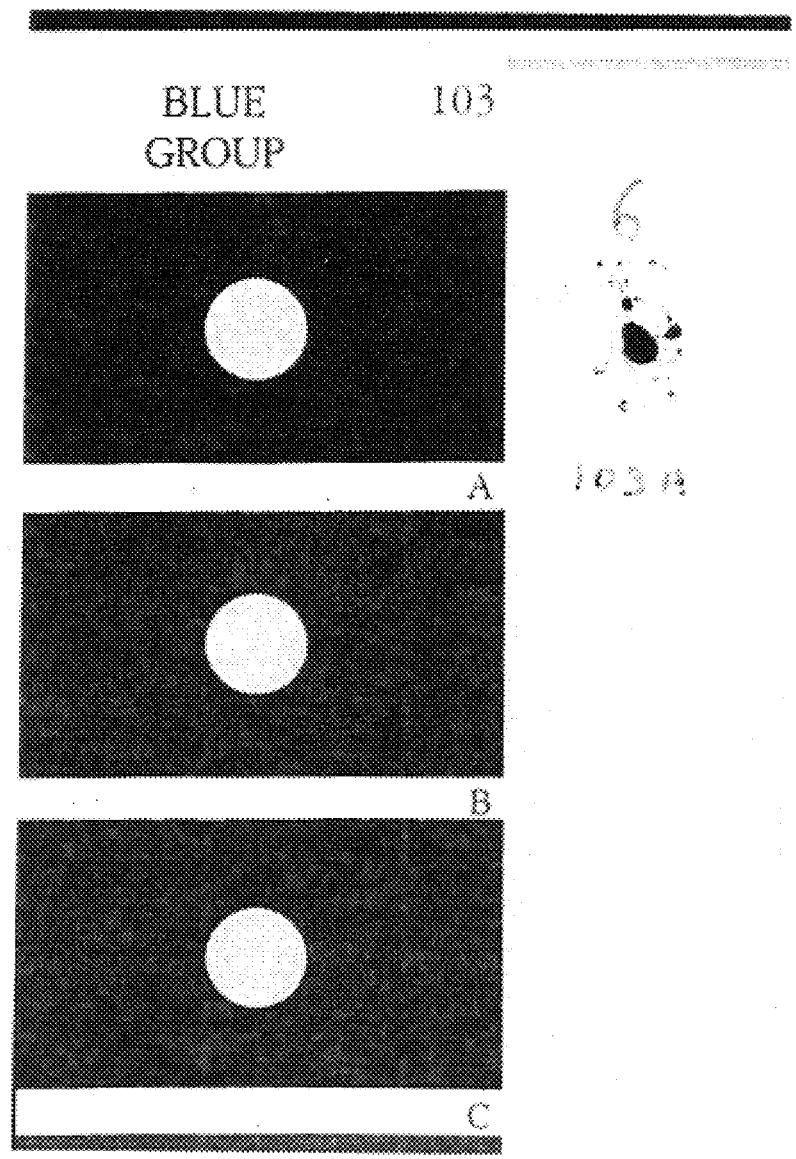
FIG. 6 represents colourant of blue group (103A).
Figure 7:
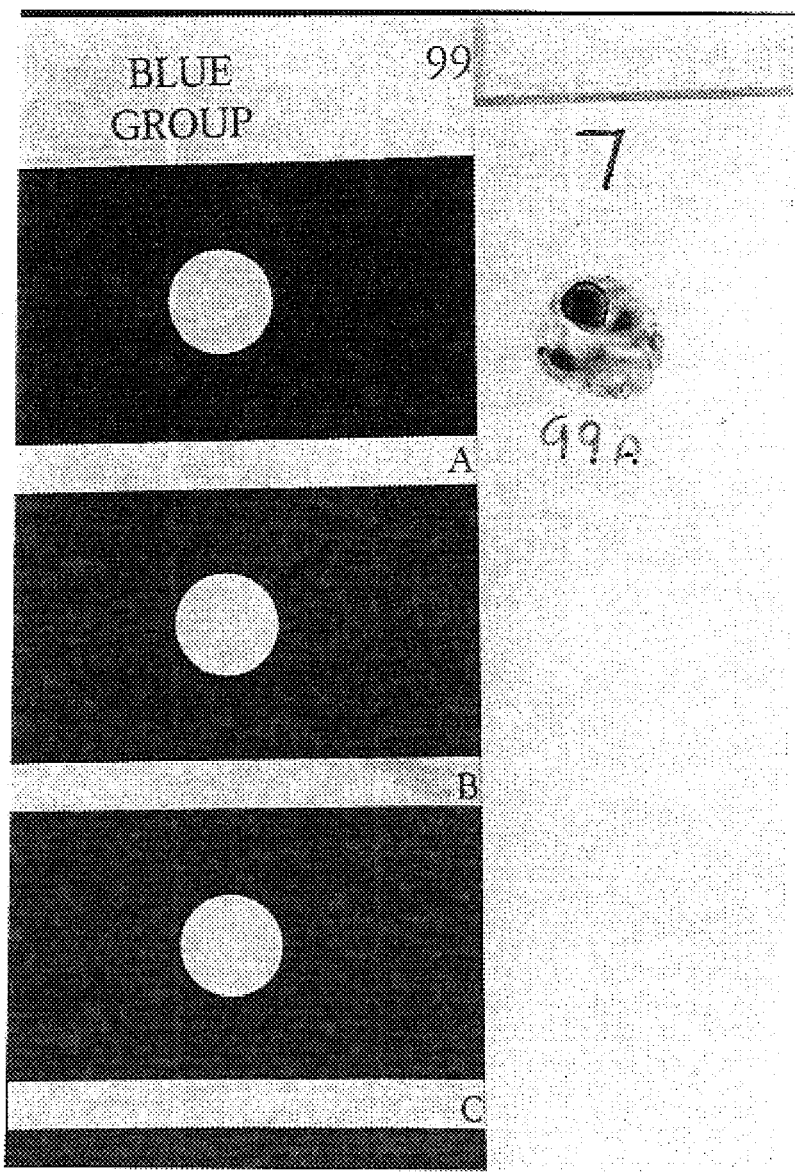
FIG. 7 represents colourant of blue group (99A).
Figure 8:
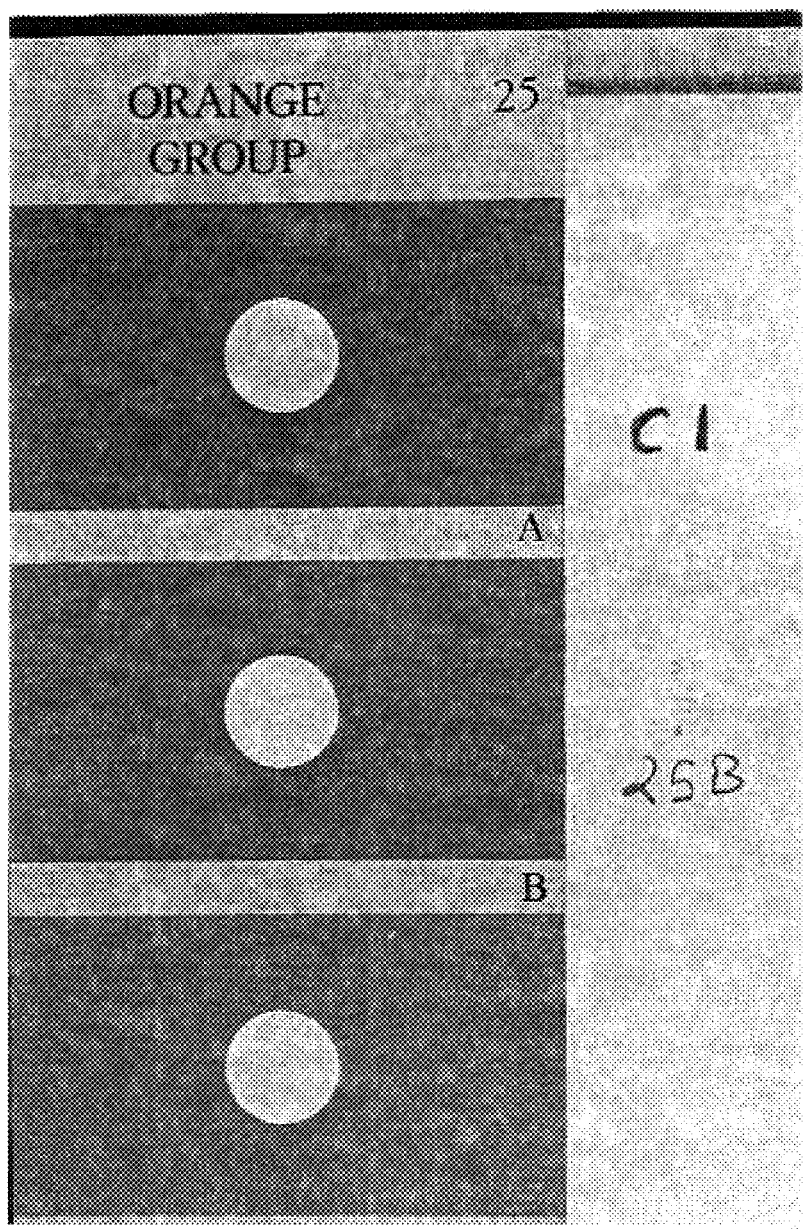
FIG. 8 represents colourant of orange group (25B).
Figure 9:
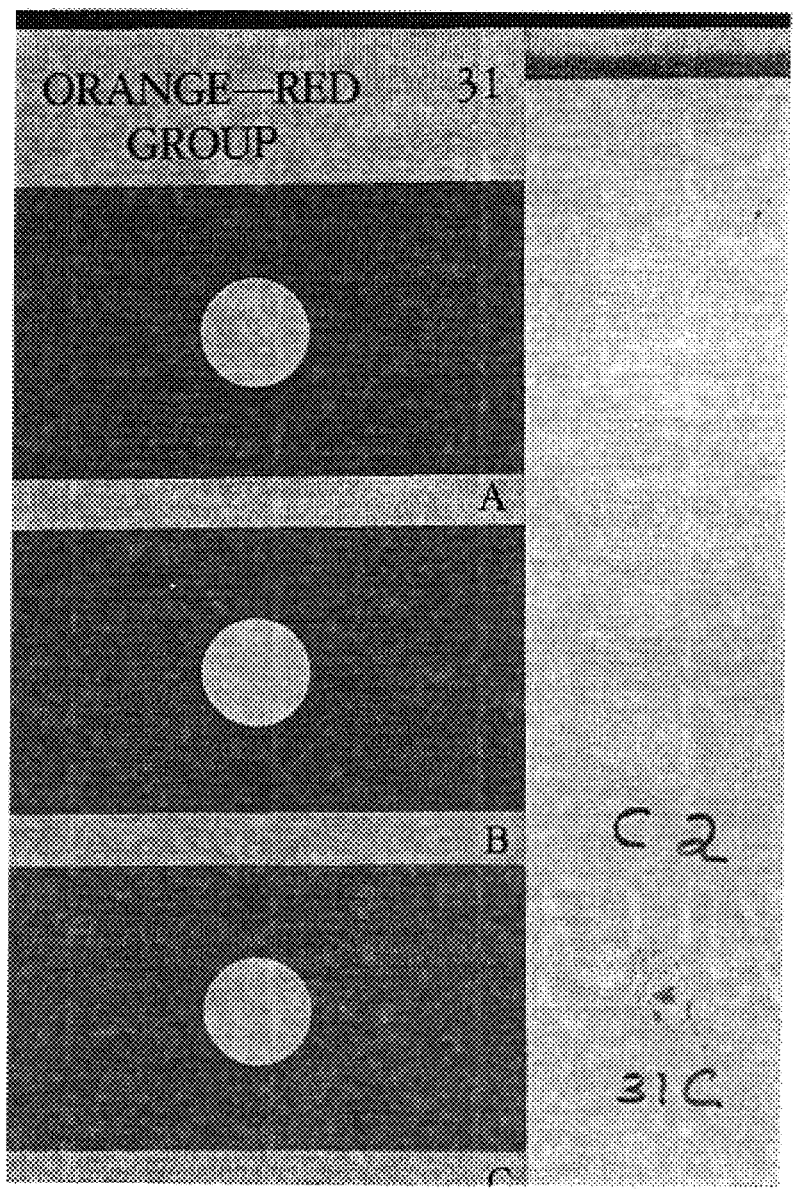
FIG. 9 represents colourant of orange red group (31C).
Figure 10:
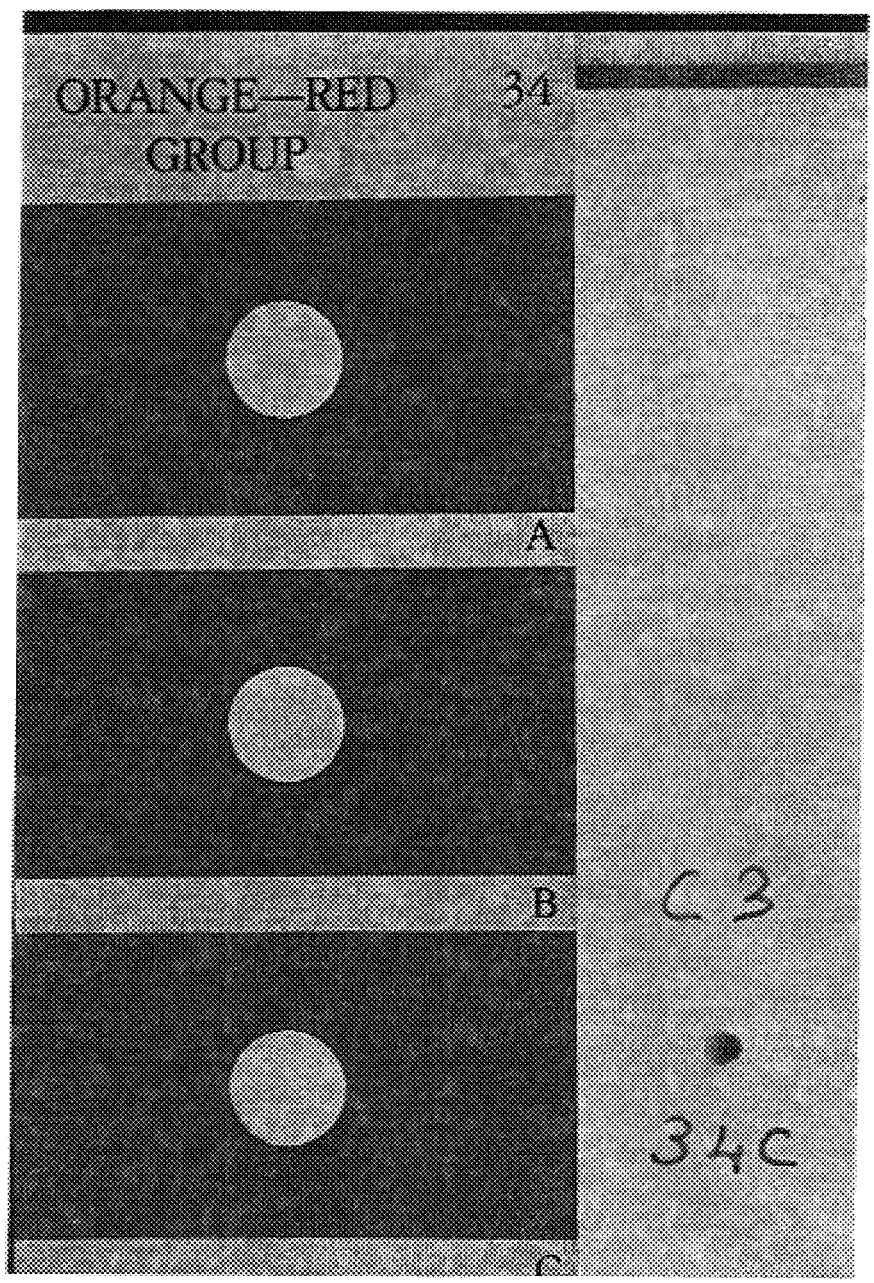
FIG. 10 represents colourant of orange red group (34C).
Figure 11:
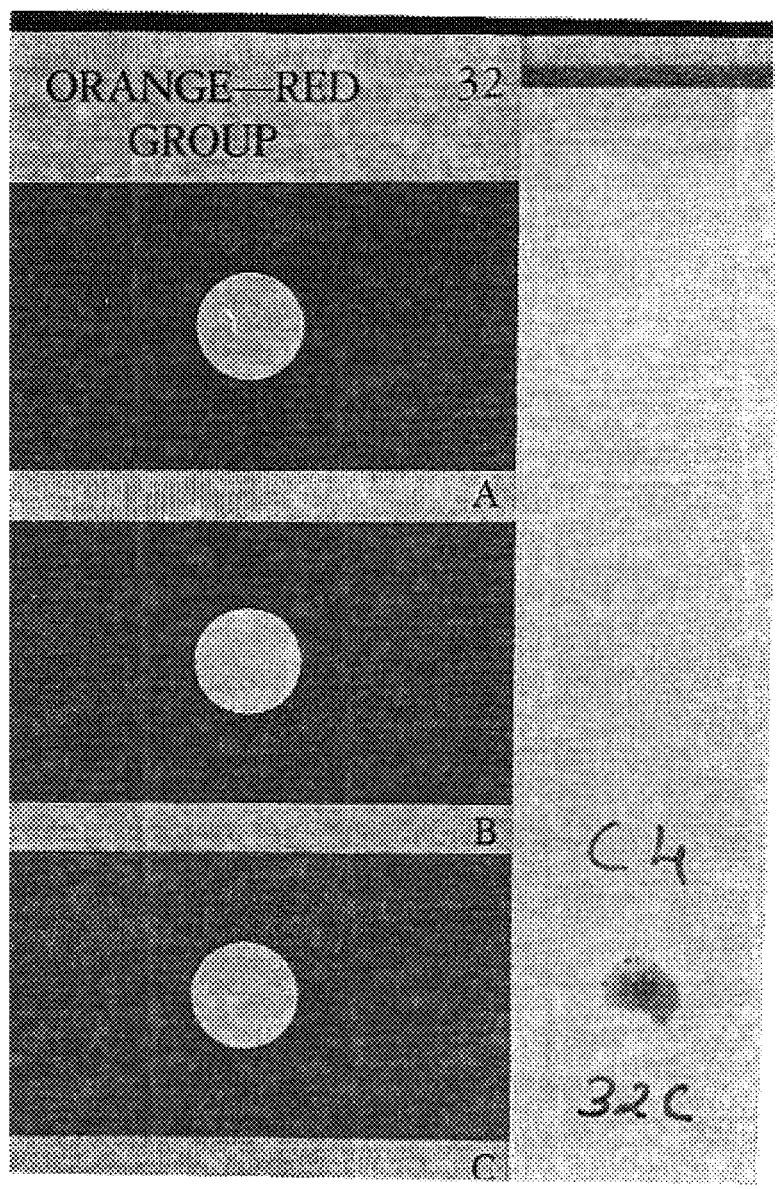
FIG. 11 represents colourant of orange red group (32C).
Figure 12:
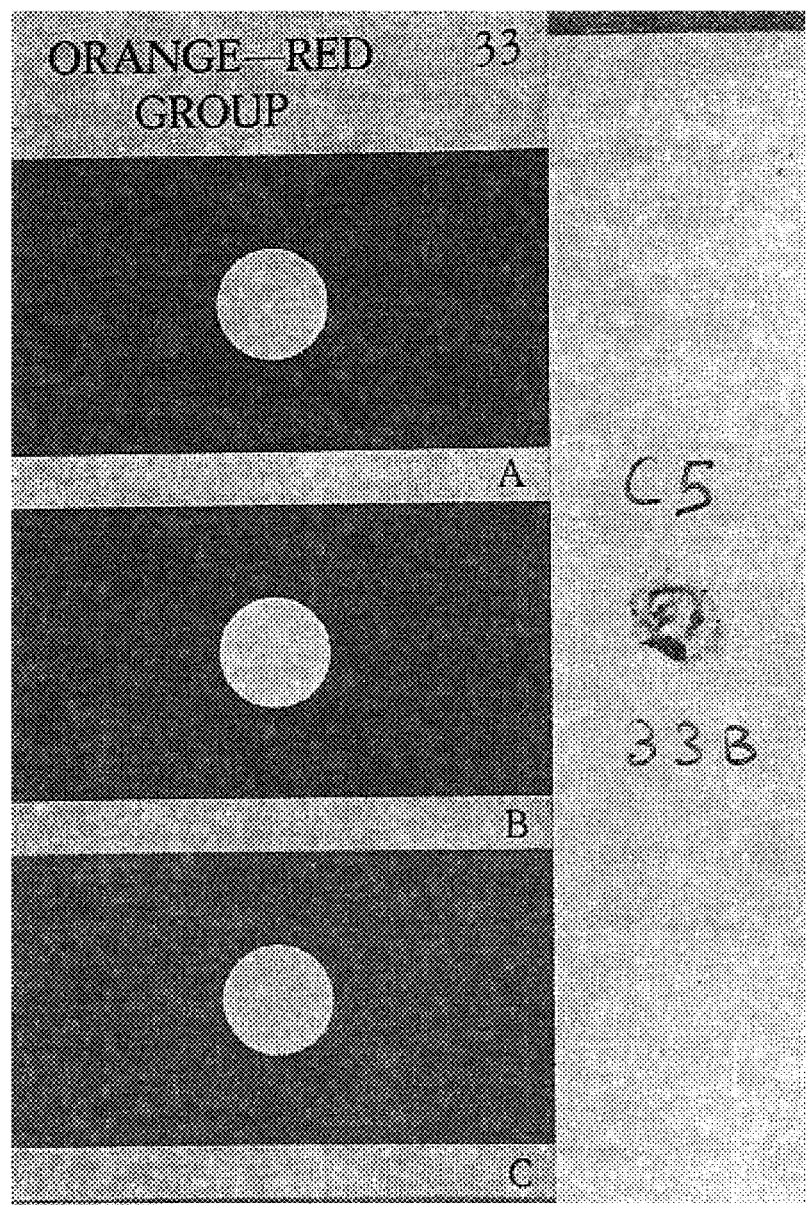
FIG. 12 represents colourant of orange red group (33B).
Figure 13:
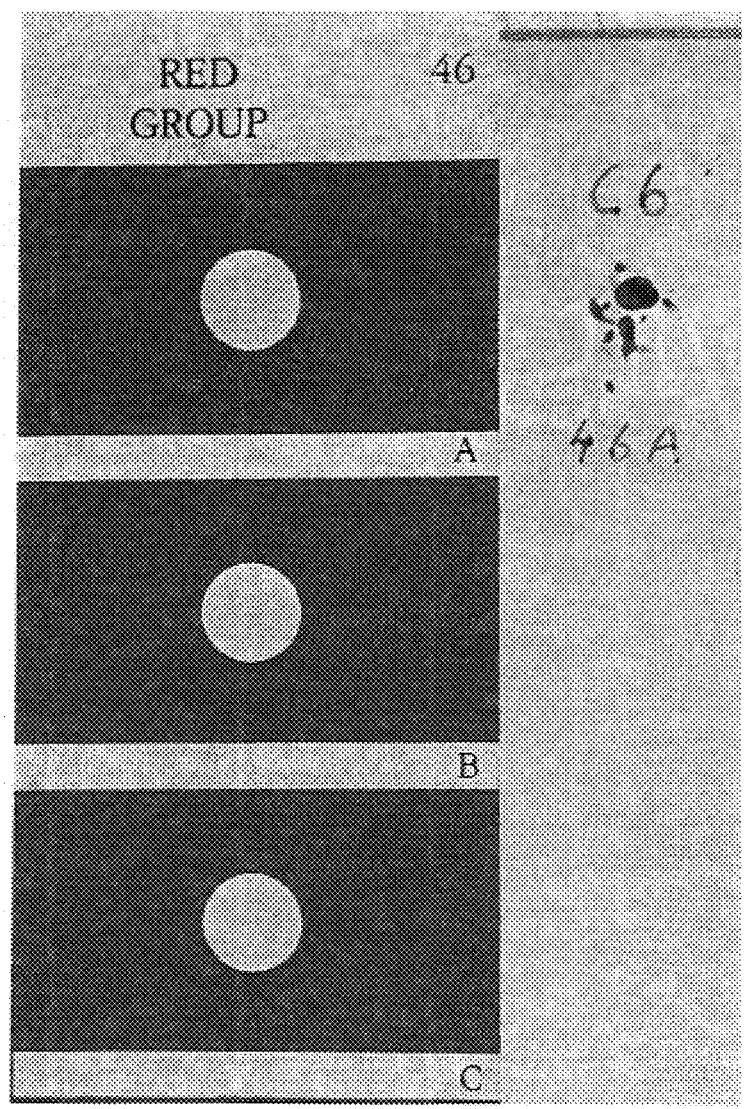
FIG. 13 represents colourant of red group (46A).
Figure 14:
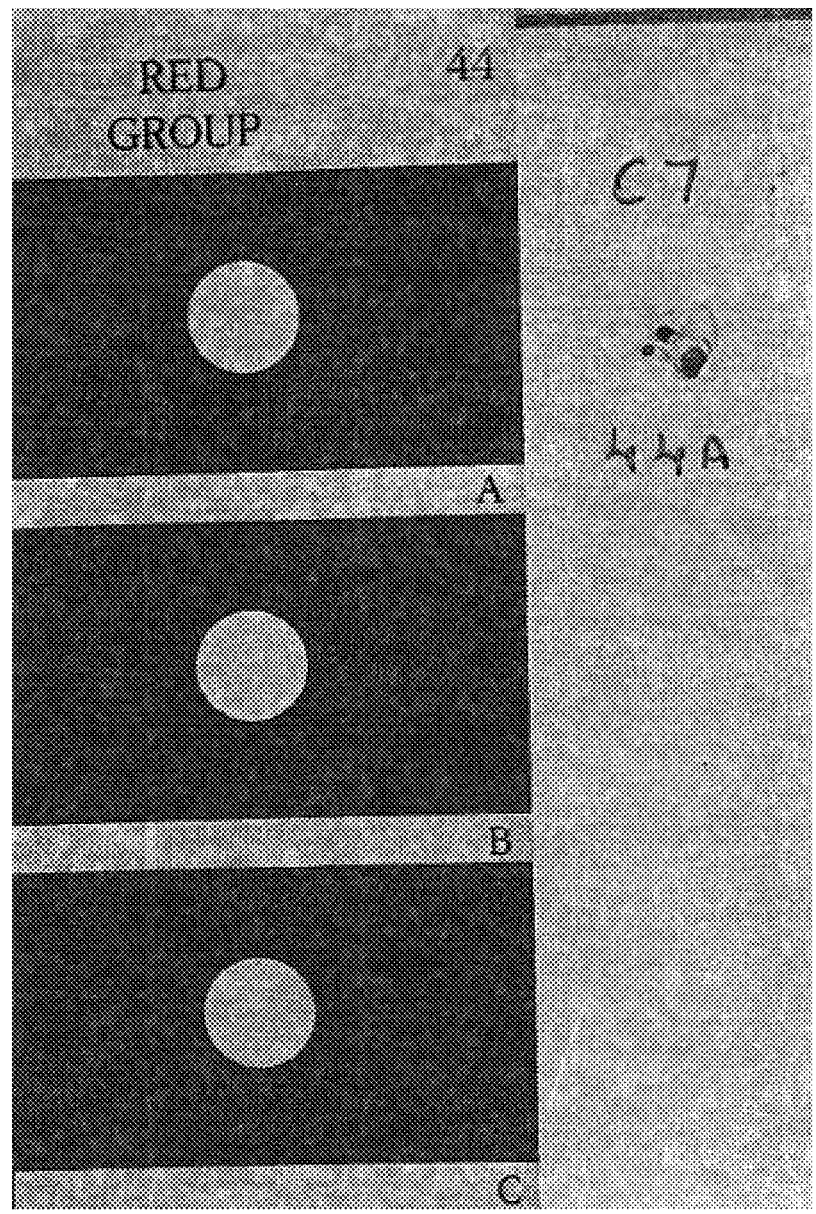
FIG. 14 represents colourant of red group (44A).
Figure 15:
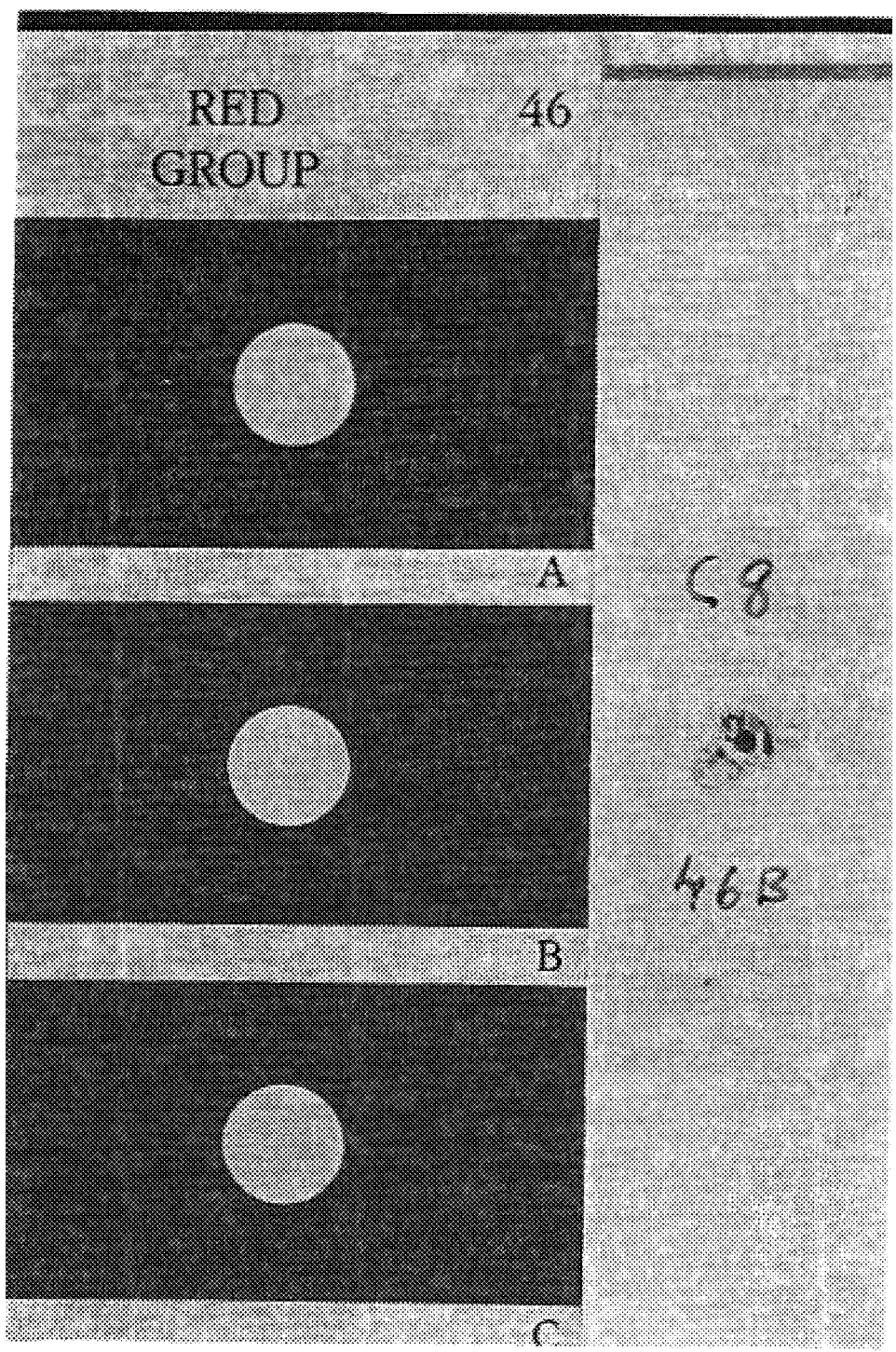
FIG. 15 represents colourant of red group (46B).
Figure 16:
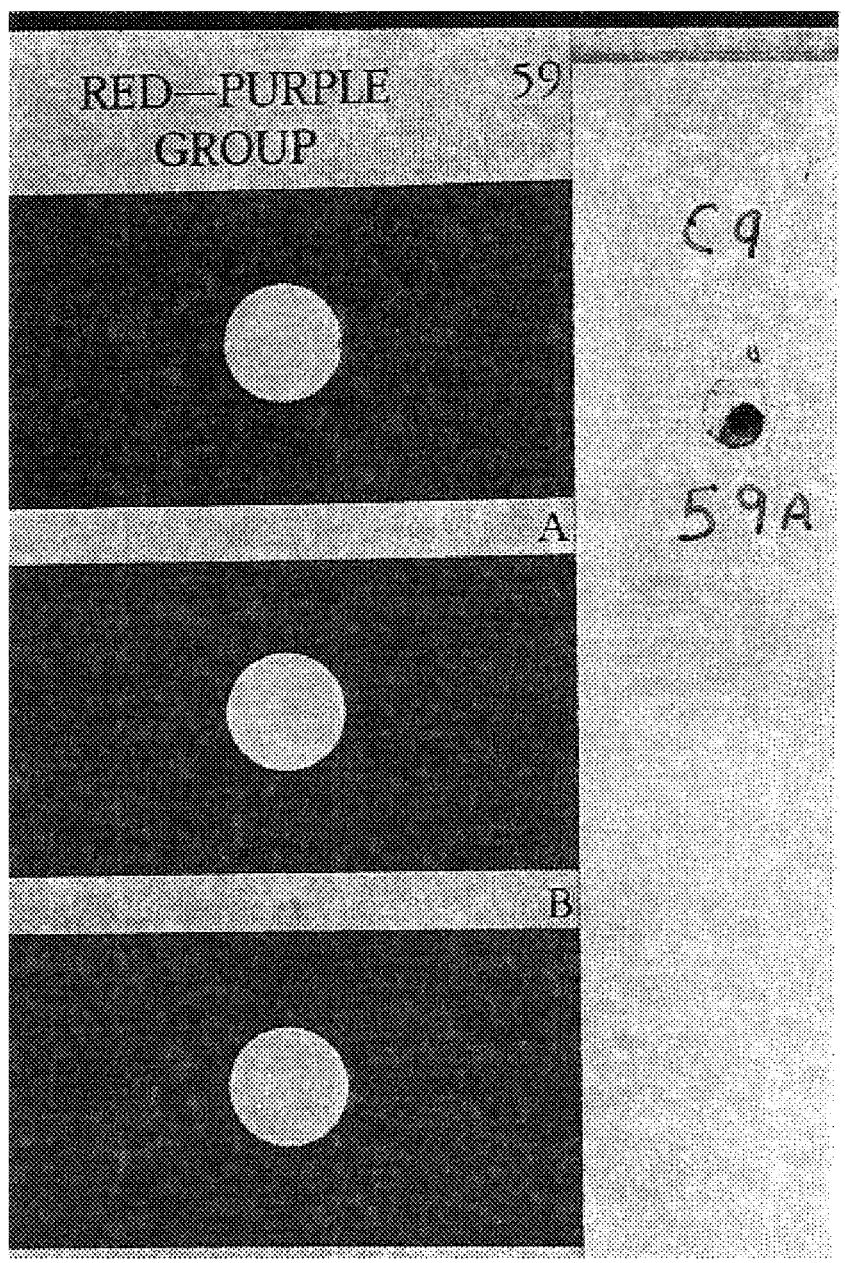
FIG. 16 represents colourant of red group (59A).
Figure 17:
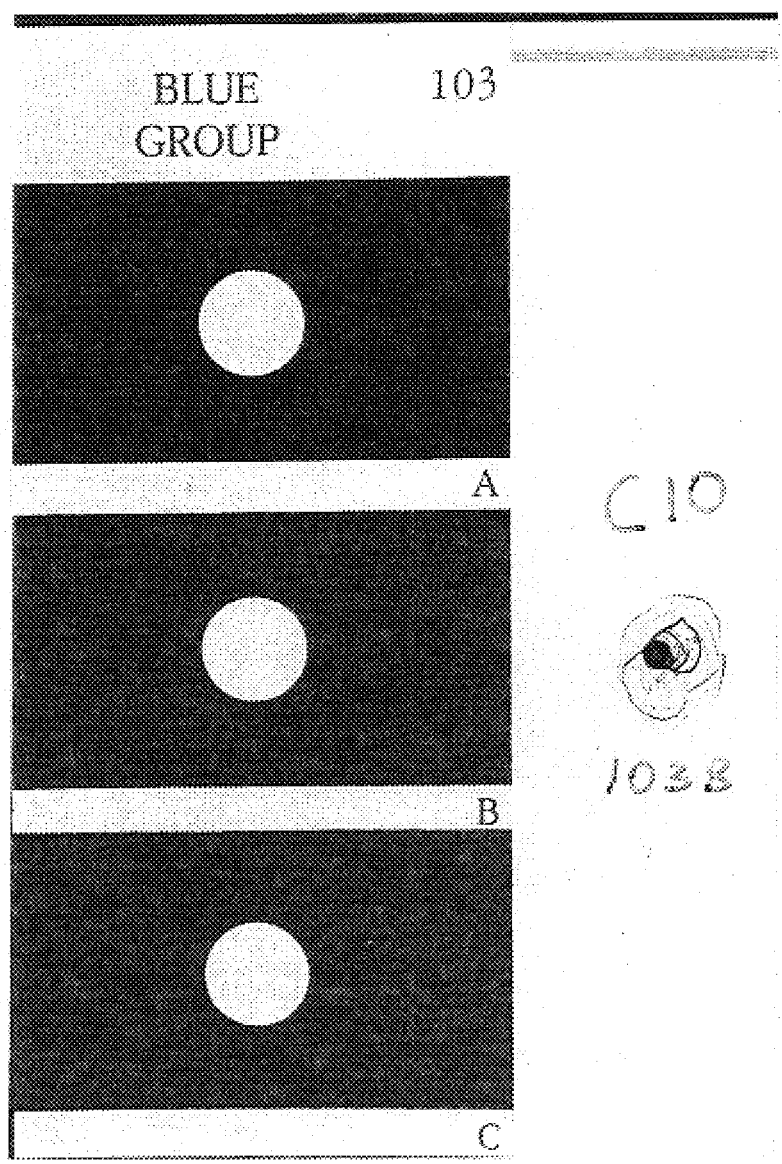
FIG. 17 represents colourant of blue group (103B).
Figure 18:
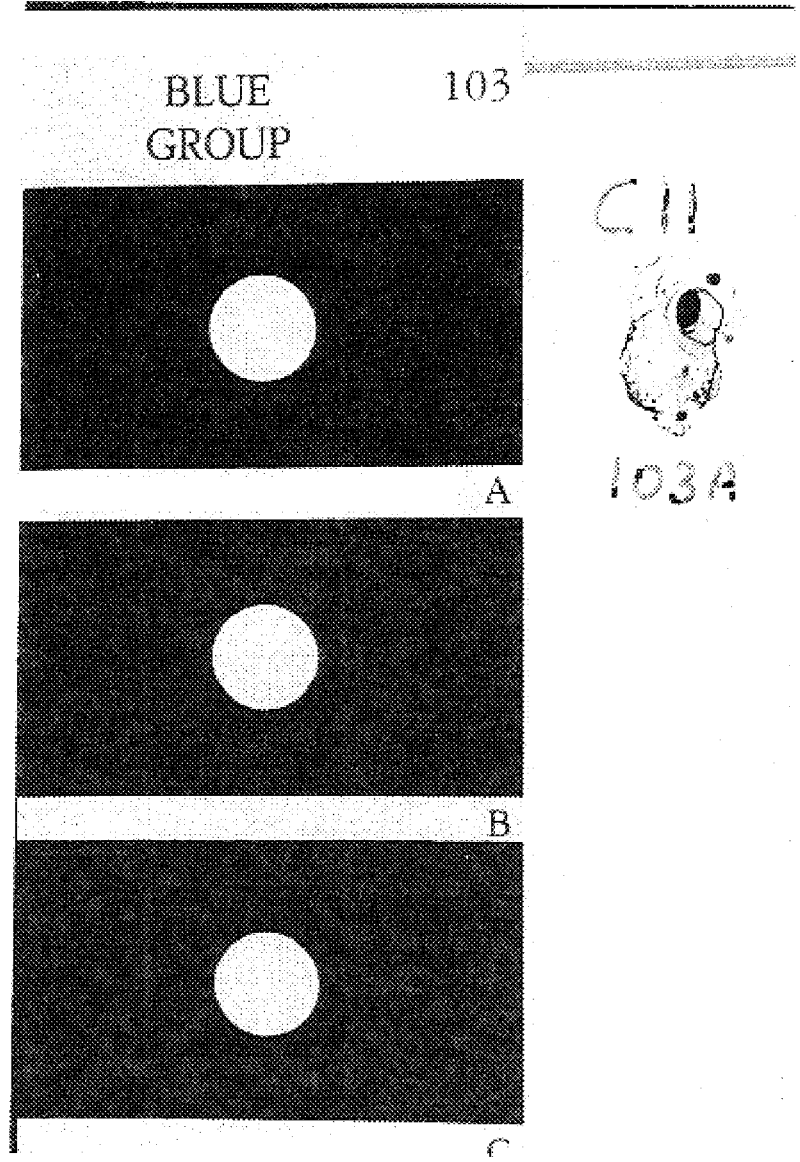
FIG. 18 represents colourant of blue group (103A).
Figure 19:
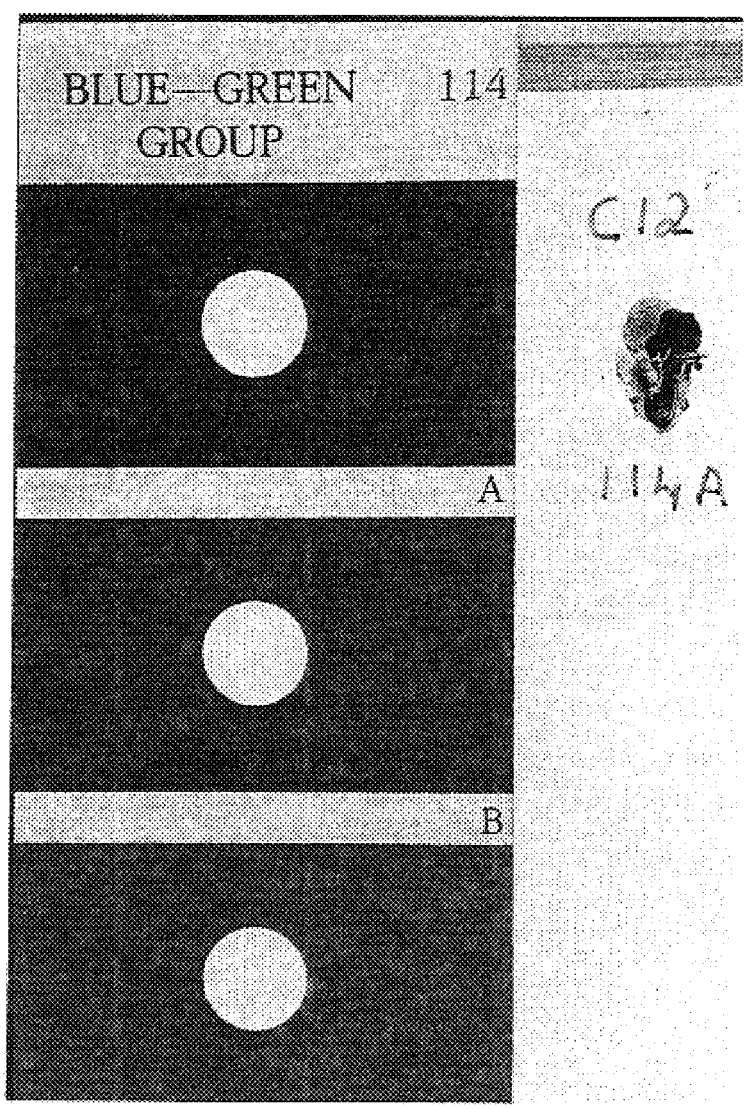
FIG. 19 represents colourant of blue-green group (114A).
Figure 20:
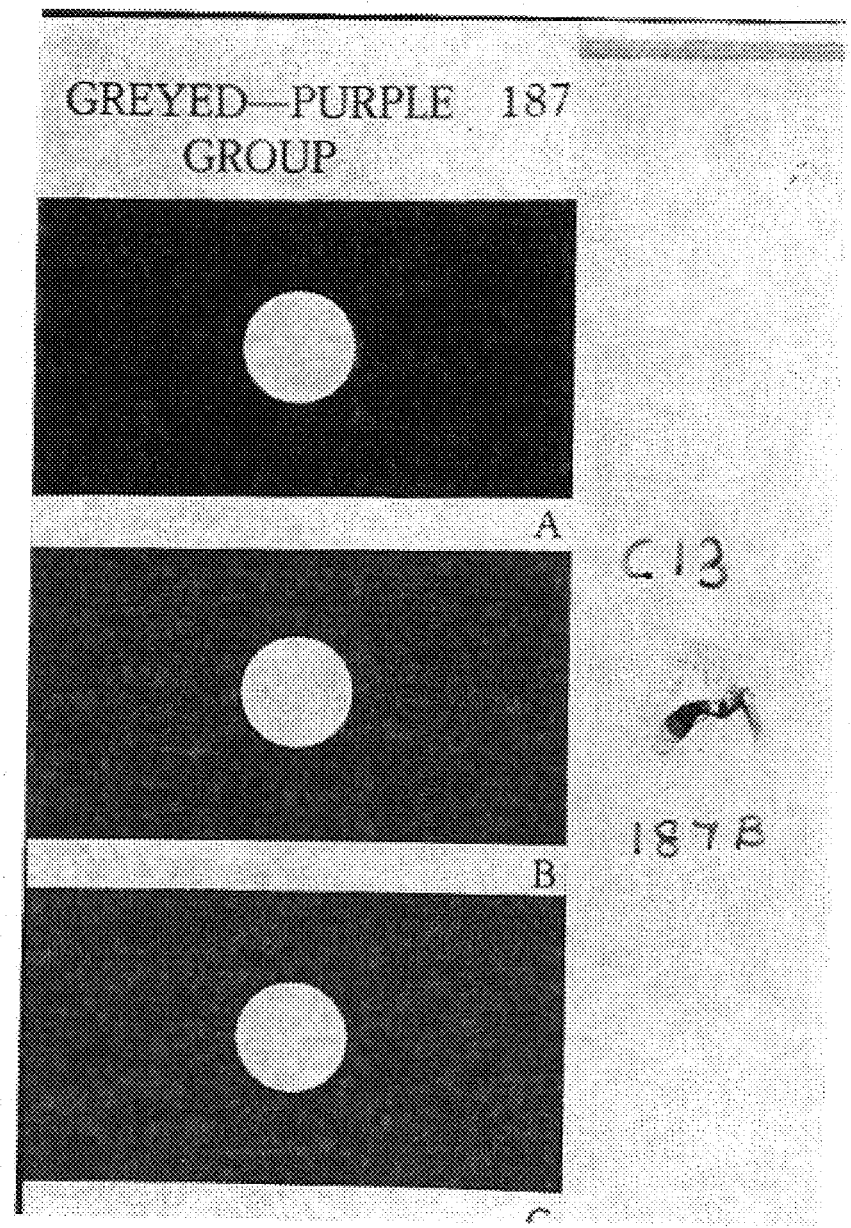
FIG. 20 represents colourant of greyed-purple group (187B).
Figure 21:
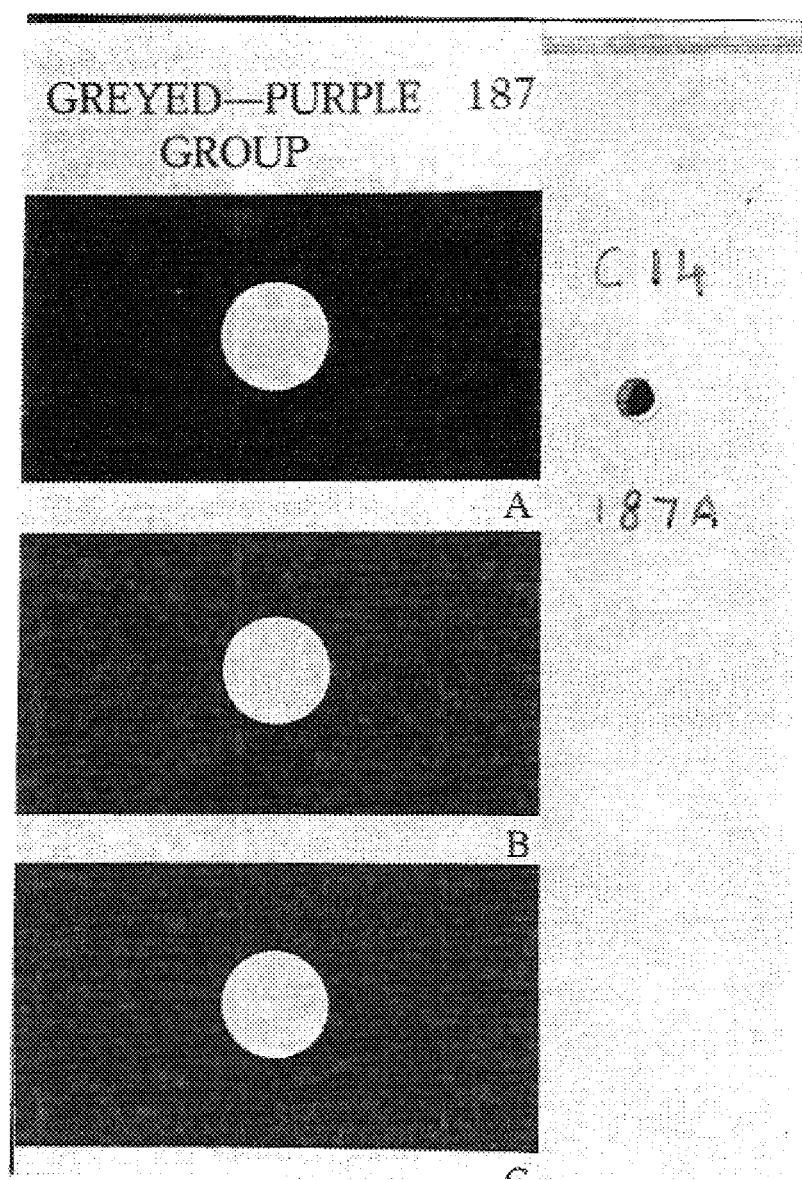
FIG. 21 represents colourant of greyed-purple group (187A).
Figure 22:
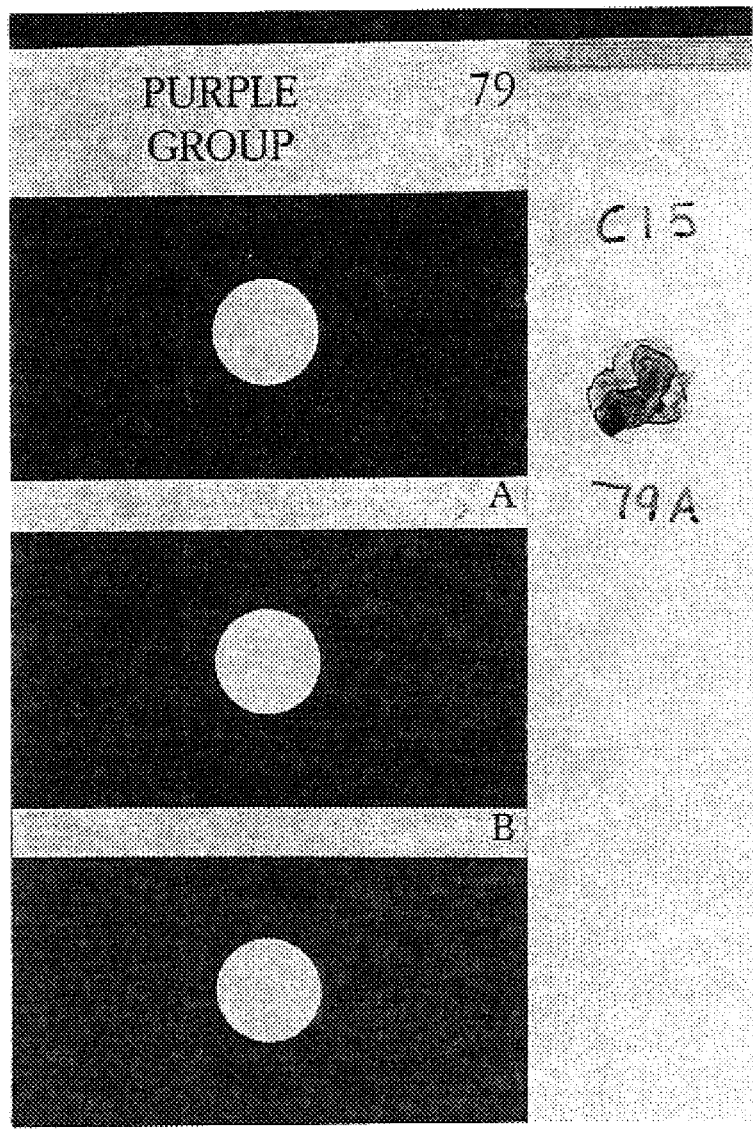
FIG. 22 represents colourant of purple group (79A).
Figure 23:
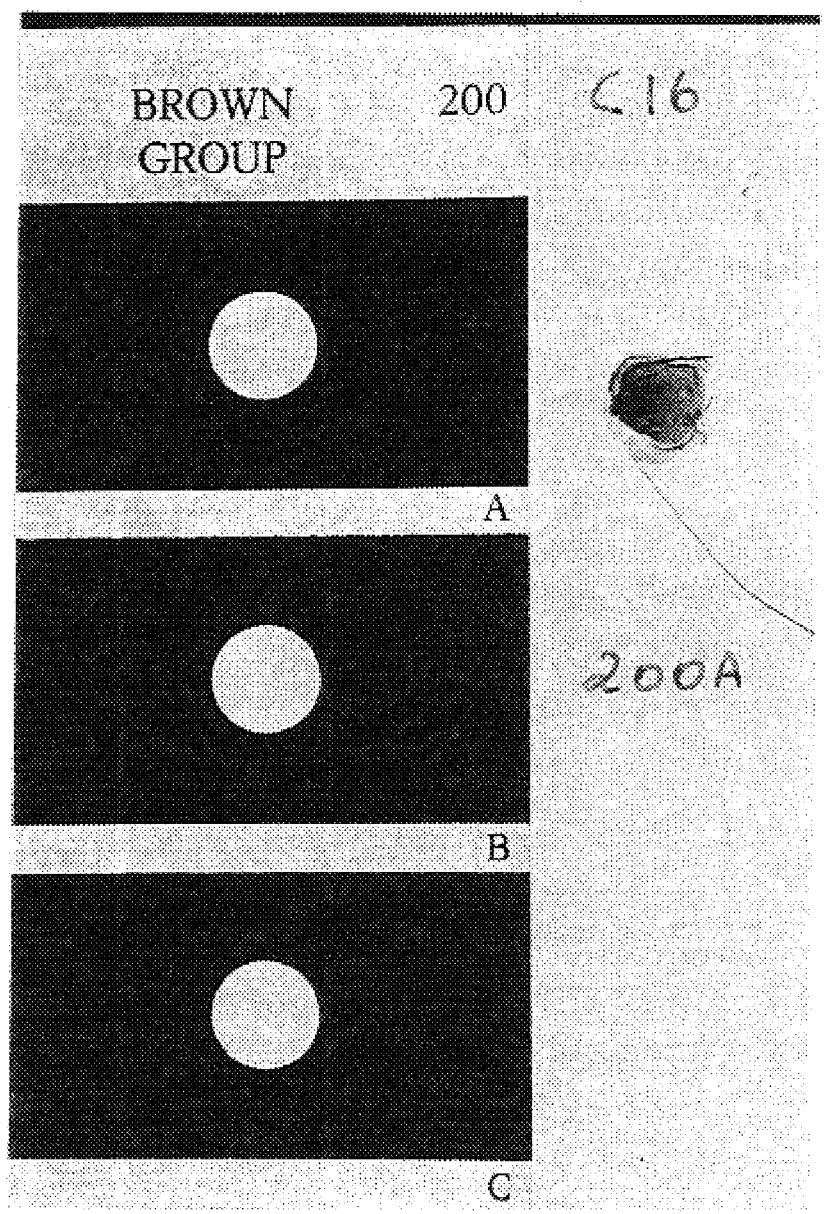
FIG. 23 represents colourant of brown group (200A).
Figure 24:
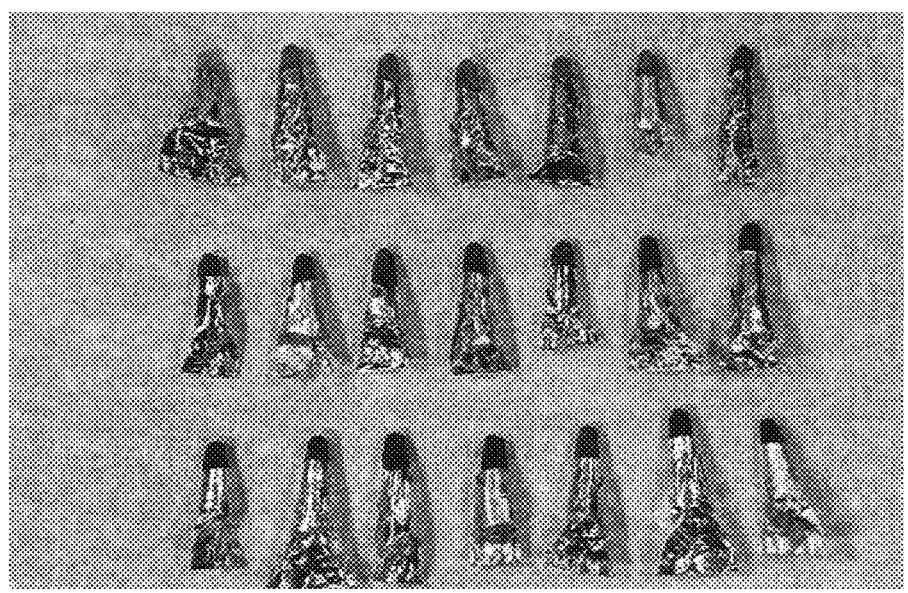
FIG. 24 depicts a few of various shades of lipsticks obtained according to the invention.

Table 1 depicts preferred list of Aroma i.e. essential oils for the functional attributes in cosmaceutical application.
Table 2 represents preferred list of Aroma isolates for the functional attributes in cosmaceutical application.
Table 3 represents change of colours obtained from direct extraction (process 1)—Change of colours with bases.
Table 4 represents change of colours obtained from direct extraction (process 1)—Change of colours with acids.
Table 5 represents change of colours obtained from column (process 2)—Change of colour with acids.
Table 6 represents change of colours obtained from column (process 2)—Change of colour with bases.
Table 7: Table for correspondence of colour codes based on Flower Council of Holland.

The various colours shown are codified according to RHS colour chart in associatiation with Flower Council of Holland and The Royal Horticultural Society, London.

The following examples are given to illustrate the invention and should not be construed to limit the scope of the present invention.

Preparation of Herbal Colourants and Lipstick:

The present invention is illustrated further by referring to the following examples. However, the present invention is not limited to these examples.

Process

Extracted the powdered material with non-polar solvents (like hexane, petroleum ether, toluene and cyclohexane) and mixtures of non-polar and polar solvents (The polar solvents are chloroform Acetone, Ethylacetate, methanol, ethanol).

The ranges of ratio of non-polar and polar solvents are 99:1 to 0:100.

The change of color by treating the color with traces of food grade acids e.g. Acetic acids less than 0.1%

The change of color with the treatment of traces of bases i.e. less than 0.1%.

EXAMPLE-1

100 gm air-dried coarsely powdered root of *Onosma* species is sieved in 40 mesh sieve and then extracted in Soxhlet apparatus with hexane at a temperature of 50° C. for 12–18 hours which resulted in the formation of hexane soluble herbal matter. The said matter was concentrated at a reduced pressure of 70 psi and at a temperature of 35° C., resulting in the yield of 6.0 gm. as the purplish red colour (Plate NO 12 A7 of Methuen handbook of colour, 1978).

EXAMPLE-2

100 gm air dried coarsely powdered stem and root in the ratio of 1:4 of *Onosma* species is sieved in 40 mesh sieve and then extracted in Soxhlet apparatus, with chloroform, at a temperature of 60° C. for 18–24 hours which resulted in the formation of chloroform soluble herbal matter. The said matter was concentrated at a reduced pressure of 80 psi and at the temperature of 40° C., resulting in the yield of 8.5 gm. as the beet-root purple (Plate No: 13 D8)

EXAMPLE-3

100 gm air dried coarsely powder stem, root and leaf in the ratio of 1:1:3 of *Macrotomia* species is percolated at room temperature with the mixture of chloroform and hexane in the ratio of 5:95 for 4 hours (3 times). Combined all the extracts and concentrated at a pressure of 70 psi and a temperature of 50° C. Thus 3.5 gm of cerise colourant (Plate No: 12 C8) was obtained.

EXAMPLE-4

100 gm air-dried coarsely powdered root of *Onosma* species is sieved in 40 mesh sieve and then extracted in Soxhlet apparatus with hexane at a temperature of 50° C. for 12–18 hours which resulted in the formation of hexane soluble herbal matter. The said matter was concentrated at a reduced pressure of 70 psi and at a temperature of 35° C., resulting in the yield of 6.0 gm. as the purplish red colour (Plate NO 12 A7) which gets changed to rose red after treatment with 1% formic acid.

EXAMPLE-5

100 gm air dried coarsely powdered stem and root in the ratio of 1:4 of *Onosma* species is sieved in 40 mesh sieve and then extracted in Soxhlet apparatus, with chloroform, at a temperature of 60° C. for 18–24 hours which resulted in the formation of chloroform soluble herbal matter. The said matter was concentrated at a reduced pressure of 80 psi and at the temperature of 40° C., resulting in the yield of 8.5 gm. as the beet-root purple (Plate No: 13 D8) which gets changed with 0.1% HCl to ruby red colour (Plate No: 12 D8).

EXAMPLE-6

100 gm air dried coarsely powder stem, root and leaf in the ratio of 1:1:3 of *Macrotomia* species is percolated at room temperature with the mixture of chloroform and hexane in the ratio of 5:95 for 4 hours (3 times). Combined all the extracts and concentrated at a pressure of 70 psi and a temperature of 50° C. Thus 3.5 gm of cerise colour (Plate No: 12 C8) was obtained which gets changed to vivid blue (Plate No: 21 A8) with the addition of the 0.1% NaO.

EXAMPLE-7

100 gm air dried coarsely powdered root of *Onosma* species is percolated with ethyl alcohol at room temperature for 24 hours (4 times). The alcohol soluble portion of stem and root was concentrated at reduced pressure of 70 psi and at a temperature of 50° C., resulting in the formation of 18 gm. of ethanol soluble concentrate. The said concentrate was mixed with 54 gm of silica gel for preparing slurry. This slurry was dried with the help of vacuum pump. The column chromatography of this dried slurry was carried out by using hexane: chloroform in the ratio of 95:5. The fractions obtained with aforesaid solvents were concentrated at the reduced pressure of 90 psi and at a temperature of 40° C., thereby giving the yield of 0.3 gm as the pastel red colour (Plate No:9 A5) which gets changed to vivid blue (Plate No: 21 A8) with the addition of the 0.1% NaOH.

Preparation of Cosmetic Compositions

The herbal colourant obtained by the process described in Examples 1 to 7 can be used according to the invention to develop various cosmetic compositions useful as lip stick, eye-liners, eye-shadows, glow-glitters and rouges. Such compositions are prepared following the general principles used in making cosmetic compositions. Specifically, the herbal colourant obtained from the plant parts is mixed with a base in appropriate proportion. The base may be liquefied first and the colourant of choice may be added and stirred. Alternatively, the colourant and the base are added, the mixture is heated, and the ingredients are stirred to obtain a homogenous mixture. To this mixture, essential oil is added together with softening agents, mood lifting agents and other additives as may be necessary for the compositions. For instance, if glow-glitters composition is to be prepared, with the basic composition, additives that provide glitter are added. The composition prepared when cooled to room temperature becomes suitable for use as a cosmetic composition.

While the above is only an outline describing the preparation of cosmetic composition, specific instances of preparing different cosmetic compositions for various applications is described in Examples 10 to 17 here below. The specific instances provided herein below are meant only to illustrate the invention and the same should not be construed to limit the scope of the invention in any manner.

EXAMPLE-8

0.5 mg of herbal colour was mixed with 1 ml of Safflower oil and 1 ml Castor oil thoroughly. In the said mixture 1.5 gm of melted bees wax was mixed at a temperature of 70° C. After that 5 microlitre tocopherol and I microlitre of *Rosamarinus* essential oil was added to the aforesaid mixture.

Then the mixture was cooled to room temperature. This cooled mixture is now ready for application.

| Substance | Amount | Percentage |
|---|---|---|
| 1. Colour | 0.5 mg | 0.5% |
| 2. Safflower oil | 1.0 ml | 1.0% |
| 3. Castor oil | 1.0 ml | 1.0% |
| 4. Tocopherol | 5 µl | 0.005% |
| 5. *Rosamarinus* (Essential oil) | 1.0 µl | 0.001% |
| 6. Bees wax | 1.5 gm | To make up 100% |

EXAMPLE-9

0.5 mg of herbal colour was mixed with 1 ml of Safflower oil and 1 ml Castor oil thoroughly. In the said mixture 1.5 gm of melted bees wax was mixed at a temperature of 70° C. After that 5 microlitre tocopherol and 1 microlitre each of *Jasminum* and *Santalum* essential oils were added to the aforesaid mixture. Then the mixture was cooled at room temperature. This cooled mixture is now ready for application.

| Substance | Amount | Percentage |
|---|---|---|
| 1. Colour | 0.1 mg | 0.5% |
| 2. Safflower oil | 1.0 ml | 1.0% |
| 3. Castor oil | 1.0 ml | 1.0% |
| 4. Tocopherol | 5.0 µl | 0.005% |
| 5. *Jasminum* and *Santalum* (Essential oil) | 1.0 µl | 0.001% |
| 6. Bees wax | 1.5 gm | To make up 100% |

EXAMPLE-10

0.5 mg of red colourant was mixed with 1 ml of safflower oil and 1 ml of castor oil thoroughly. In the said mix, 0.5 gm of melted bees was mixed at a temperature of 70° C. After that 5 microliter tocopheral and 1 microlitre of sandal wood oil was added to the aforesaid mixture. Then the mixture was cooled to room temperature. Thus, cooled mixture is ready for application as eye shadows.

| Substance | Amount | Percentage |
|---|---|---|
| 1. Colour | 0.5 mg | 0.5% |
| 2. Safflower oil | 1.0 ml | 1.0% |
| 3. Castor oil | 1.0 ml | 1.0% |
| 4. Tocopherol | 5.0 µl | 0.005% |
| 5. Sandal wood oil (Essential oil) | 1.0 µl | 0.001% |
| 6. Bees wax | 0.5 gm | To make up 100% |

EXAMPLE-11

1.0 mg of herbal colour was mixed with 1 ml of safflower oil and 1 ml of castor oil thoroughly. Then mixed 0.2 gm of melted bees wax at a temperature of 70° C. After that 10 microliter tocopherol and 2 microlitre of Rose oil was added to the aforesaid mixture. Then the mixture was cooled to room temperature. Thus, cooled mixture is ready for application as glow-glitters.

| Substance | Amount | Percentage |
|---|---|---|
| 1. Colour | 1.0 mg | 1.0% |
| 2. Safflower oil | 1.0 ml | 1.0% |
| 3. Castor oil | 1.0 ml | 1.0% |
| 4. Tocopherol | 1.0 µl | 0.01% |
| 5. Rose oil (Essential oil) | 2.0 µl | 0.002% |
| 6. Bees wax | 0.2 gm | To make up 100% |

EXAMPLE-12

0.25 mg of rose red colourant was mixed with 10 gm talc in ball mill. In said mixture 1 microliter of Jasmine essential oil was added and mixed thoroughly. The colorant mixed is now ready for rouges.

| Substance | Amount | Percentage |
|---|---|---|
| 1. Colour | 0.25 mg | 0.25% |
| 2. Jasmine (Essential oil) | 1.0 µl | 0.001% |
| 3. Talc | 10.0 gm | To make up 100% |

EXAMPLE-13 (Antidepressant Activity)

0.5 mg of herbal colour was mixed with 1 ml of Safflower oil and 1 ml Castor oil thoroughly. In the said mixture 1.5 gm of melted bees wax was mixed at a temperature of 70° C. After that 5 microlitre tocopherol and 1 microlitre blend of sweet basil oil (having linaloal and linolyl acetate), Jasminum and lemon grass oil/citral essential oil was added to the aforesaid mixture. Then the mixture was cooled to room temperature. This cooled mixture is now ready for application.

| Substance | Amount | Percentage |
|---|---|---|
| 1. Colour | 1.5 mg | 1.0% |
| 2. Safflower oil | 1.0 ml | 1.0% |
| 3. Castor oil | 1.0 ml | 1.0% |
| 4. Tocopherol | 10 µl | 0.01% |
| 5. Sweet basil oil, Jasmine and lemon grass oil | 2.0 µl | 0.002% |
| 6. Bees wax | 1.5 gm | To make up 100% |

EXAMPLE-14 (Mood Lifting)

1.5 mg of herbal colour was mixed with 1 ml of Safflower oil and 1 ml Castor oil thoroughly. In the said mixture 1.5 gm of melted bees wax was mixed at a temperature of 70° C. After that 5 microlitre tocopherol and 1 microlitre blend of Jasmine, Muskon oil and lavender oil essential oil was added to the aforesaid mixture. Then the mixture was cooled to room temperature. This cooled mixture is now ready for application.

| Substance | Amount | Percentage |
|---|---|---|
| 1. Colour | 1.5 mg | 1.0% |
| 2. Safflower oil | 1.0 ml | 1.0% |

-continued

| Substance | Amount | Percentage |
|---|---|---|
| 3. Castor oil | 1.0 ml | 1.0% |
| 4. Tocopherol | 10 µl | 0.01% |
| 5. Jasmine, Muskon oil and Lavender oil (Essential oil) | 2.0 µl | 0.002% |
| 6. Bees wax | 1.5 gm | To make up 100% |

EXAMPLE-15 (Lipstick for Men)

1 ml of Safflower oil and 1 ml Castor oil thoroughly. In the said mixture 1.5 gm of melted bees wax was mixed at a temperature of 70° C. After that 5 microlitre tocopherol and 1 microlitre blend of sandal wood oil and basil oil was added to the aforesaid mixture. Then the mixture was cooled to room temperature. This cooled mixture is now ready for application.

| Substance | Amount | Percentage |
|---|---|---|
| 1. Safflower oil | 1.0 ml | 1.0% |
| 2. Castor oil | 1.0 ml | 1.0% |
| 3. Tocopherol | 10 µl | 0.01% |
| 4. Sandal wood oil or basil oil (Essential oil) | 2.0 µl | 0.002% |
| 5. Bees wax | 1.5 gm | To make up 100% |

TABLE 1

Preferred list of Aroma i.e essential oils for the functional attributes in cosmaceutical application

| FUNCTIONAL ATTRIBUTES | ESSENTIAL OILS | PREFERRED RATIO |
|---|---|---|
| 1. Antidepressant | 1. *Ocimum* oil: *Jasminum* oil: *Cymbopogon* oil | (1:2:1) |
| | 2. *Ocimum* oil: *Mentha* oil: *Rosmarinus* oil | (2:1:1) |
| | 3. *Jasminum* oil: *Mentha* oil: *Rosmarinus* oil | (1:1:1) |
| | 4. *Cymbopogon* oil: *Ocimum* oil: *Mentha* oil | (1:2:1) |
| | 5. *Ocimum* oil: *Cymbopogon* oil | (2:1) |
| | 6. *Mentha* oil: *Rosmarinus* oil | (1:1) |
| | 7. *Ocimum* oil | |
| | 8. *Rosmarinus* oil | |
| 2. Anti stress | 1. *Santalum* oil: *Lavandula* oil | (2:1) |
| | 2. *Lavandula* oil: *Eucalyptus* oil: *Rosa* oil | (1:1:1) |
| | 3. *Eucalyptus* oil: *Rosa* oil | (1:2) |
| | 4. *Aluillaria* oil: *Elettaria* oil: *Rosmarinus* oil | (1:1:1) |
| | 5. *Jasminum* oil | |
| | 6. *Santalum* oil | |
| | 7. *Lavandula* oil | |
| 3. Refreshing | 1. *Santalum* oil: *Rosa* oil: *Rosmarinus* oil | (1:1:1) |
| | 2. *Santalum* oil: *Pelargonium* oil | (1:2) |
| | 3. *Jasminum* oil: *Lavandula* oil | (1:2) |
| | 4. *Lavandula* oil | |
| | 5. *Santalum* oil: *Rosa* oil | (1:2) |
| | 6. *Santalum* oil | |
| 4. Sensual Feeling | 1. *Jasminum* oil: *Lavandula* oil: *Pelargonium* oil | (1:2:1) |
| | 2. *Ocimum* oil: *Jasminum* oil: *Cymbopogon* oil | (1:2:1) |
| | 3. *Jasminum* oil | |
| | 4. *Jasminum* oil: *Lavandula* oil | (2:1) |
| 5. Creative Thoughts | 1. *Santalum* oil | |
| | 2. *Santalum* oil: *Rosa* oil | (1:2) |
| 6. Mood lifting | 1. *Jasminum* oil: *Rosa* oil: *Pelargonium* oil | (1:2) |
| | 2. *Rosmarinus* oil | |
| | 3. *Cymbopogan* oil: *Rosa* oil | (2:1) |
| | 4. *Rosa* oil | |
| | 5. *Jasminum* oil: *Rosa* oil | |
| 7. Anxiety | 1. *Rosa* oil: *Cinnamomum* oil | (1:2) |

TABLE 2

Preferred list of Aroma isolates for the functional attributes in cosmaceutical application.

| FUNCTIONAL ATTRIBUTES | AROMA ISOLATE | PREFERRED RATIO |
|---|---|---|
| 1. Anti stress | Citral | |
| 2. Refreshing | 1. Linalol | |
| | 2. Benzyl alcohol | |
| | 3. Terpeneol | |
| | 4. Terpeneol: Linalol | (1:2) |
| 3. Sensual Feeling | Butyric acid | |

TABLE 2-continued

Preferred list of Aroma isolates for the functional attributes in cosmaceutical application.

| FUNCTIONAL ATTRIBUTES | AROMA ISOLATE | PREFERRED RATIO |
|---|---|---|
| 4. Creative Thoughts | 1. Isobutyric acid: Butyric acid: linalol | (1:2:1) |
| | 2. Isobutyric acid: Benzyl alcohol: linalol | (1:2:1) |
| | 3. Isobutyric acid: | |
| | 4. Linalol: Isobutyric acid | (1:2) |
| 5. Mood lifting | 1. Jasmone | |
| | 2. Citral | |
| | 3. Eugenol | |
| | 4. Citral | |
| | 5. Eugenol: Citral | (1:2) |

The change in color of the colourants, occurs then they are subjected to acid or base treatments. For example, change of colour occurs by treating the colourant with traces of food grade acids example acetic acid at a quantum less than 0.1%, likewise, the change of colour occurs with the treatment of base which can be as traces as less than 0.1%.

The following four tables provide information about the color changes change occur due to acid or base treatments.

TABLE 3

DIRECT EXTRACTION (PROCESS 1) Change of colour with bases

| | | Sodium Hydroxide | | | Potassium Hydroxide | | | Sodium acetate | | |
|---|---|---|---|---|---|---|---|---|---|---|
| Code | Colours | 2% | 0.1% | 0.05% | 2% | 0.1% | 0.05% | 2% | 0.1% | 0.05% |
| 1. | 58C | 95A | 98B | 98B | 98B | 99C | 100B | 80D | 97B | 97C |
| 2. | 55A | 101A | 100D | 100B | 105D | 94B | 93D | 82A | 97C | 97D |
| 3. | 58B | 101B | 100B | 100D | 101D | 93B | 93C | 80C | 97B | 97D |
| 4. | 55B | 95B | 97D | 100C | 107A | 99C | 100B | 80D | 97C | 97D |
| 5. | 55C | 98A | 98C | 98D | 101B | 92B | 92D | 80B | 97D | 97D |
| 6. | 115B | 115B | 114B | 94C | 115A | 114B | 95D | 201B | 97D | 114D |
| 7. | 115A | 115A | 113C | 113C | 114D | 113C | 115B | 116B | 111B | 113C |
| 8. | 122A | 122A | 187B | 187C | 122B | 187C | 200D | 201A | 183C | 182A |

TABLE 4

DIRECT EXTRACTION (PROCESS 1) Change of colour with acids

| | | Acetic acid | | | Citric acid | | | Oxalic acid | | |
|---|---|---|---|---|---|---|---|---|---|---|
| Code | Colours | 2% | 0.1% | 0.05% | 2% | 0.1% | 0.05% | 2% | 0.1% | 0.05% |
| 1. | 58C | 46C | 73B | 65B | 46B | 55B | 56A | 47D | 48D | 49A |
| 2. | 55A | 55C | 68C | 69A | 51A | 55C | 56A | 51B | 52C | 52D |
| 3. | 58B | 73D | 75D | 75D | 73C | 38A | 39C | 73A | 69A | 69A |
| 4. | 55B | 73B | 73D | 73D | 73C | 73D | 69A | 73A | 69B | 69B |
| 5. | 55C | 70D | 68D | 69A | 73D | 69A | 69B | 68D | 38A | 38B |
| 6. | 115B | 95C | 94B | 94C | 96B | 95C | 95D | 97B | 97D | 97D |
| 7. | 115A | 115B | 113C | 133C | 116C | 115A | 115B | 113A | 111B | 111B |
| 8. | 122A | 200A | 200C | 200C | 200B | 200C | 200D | 183D | 183C | 182A |

TABLE 5

From Column (PROCESS 2) Change of colour with acids

| | | Acetic acid | | | Citric acid | | | Oxalic acid | | |
|---|---|---|---|---|---|---|---|---|---|---|
| Code | Colours | 2% | 0.1% | 0.05% | 2% | 0.1% | 0.05% | 2% | 0.1% | 0.05% |
| $C_1$ | 25B | 25C | 24A | 24A | 24A | 24C | 24C | 24A | 24C | 24A |
| $C_2$ | 31C | 29B | 29C | 29C | 27A | 27B | 27B | 29B | 29C | 27B |
| $C_3$ | 34C | 33A | 33C | 33C | 33A | 33C | 33D | 33A | 33C | 33C |
| $C_4$ | 32C | 29A | 28C | 28D | 29A | 28D | 28D | 29A | 28C | 28D |

TABLE 5-continued

From Column (PROCESS 2)
Change of colour with acids

| | | Acetic acid | | | Citric acid | | | Oxalic acid | | |
|---|---|---|---|---|---|---|---|---|---|---|
| Code | Colours | 2% | 0.1% | 0.05% | 2% | 0.1% | 0.05% | 2% | 0.1% | 0.05% |
| $C_5$ | 33B | 40C | 39C | 39D | 31B | 30C | 30D | 31C | 31D | 31D |
| $C_6$ | 46A | 46A | 45C | 45D | 32A | 31B | 30C | 33B | 32A | 32B |
| $C_7$ | 44A | 43A | 40B | 40C | 45D | 42A | 42B | 45C | 44B | 44C |
| $C_8$ | 46B | 47B | 47D | 47D | 47B | 48A | 48B | 46C | 46A | 46D |
| $C_9$ | 59A | 60A | 59D | 57D | 59B | 59D | 59D | 60B | 60C | 59C |
| $C_{10}$ | 95A | 95C | 94B | 94C | 96B | 95C | 95D | 97B | 97D | 97D |
| $C_{11}$ | 103A | 200A | 200C | 200C | 187A | 187C | 187D | 187A | 187C | 187C |
| $C_{12}$ | 114A | 115B | 113C | 113C | 116C | 115A | 115B | 113A | 111B | 111B |
| $C_{13}$ | 187B | 182A | 180C | 180D | 182C | 181D | 181D | 180B | 181C | 181D |
| $C_{14}$ | 187A | 59A | 60B | 60C | 59B | 58A | 58C | 59D | 58D | 58C |
| $C_{15}$ | 79A | 187A | 183A | 183C | 187B | 187B | 185C | 182C | 181D | 181D |
| $C_{16}$ | 200A | 200A | 200C | 200C | 200B | 200C | 200D | 183D | 183C | 182A |

TABLE 6

From Column (PROCESS 2)
Change of colour with bases

| | | NaOH | | | KOH | | | $CH_3COONa$ | | |
|---|---|---|---|---|---|---|---|---|---|---|
| Code | Colours | 2% | 0.1% | 0.05% | 2% | 0.1% | 0.05% | 2% | 0.1% | 0.05% |
| $C_1$ | 25B | 90A | 89A | 24A | 92A | 89C | 24C | 181B | 24C | 89D |
| $C_2$ | 31C | 106B | 106D | 29C | 98B | 105D | 27B | 58C | 29C | 105D |
| $C_3$ | 34C | 86C | 33C | 33C | 83B | 83C | 33D | 171C | 33C | 83D |
| $C_4$ | 32C | 93B | 93D | 28D | 102A | 99C | 28D | 169C | 28C | 93C |
| $C_5$ | 33B | 98B | 98C | 39D | 105C | 98C | 30D | 169B | 31D | 99C |
| $C_6$ | 46A | 103C | 102C | 45D | 98B | 102D | 30C | 34B | 32A | 101C |
| $C_7$ | 44A | 102B | 102C | 40C | 116A | 102D | 42B | 40A | 44B | 102D |
| $C_8$ | 46B | 116B | 116D | 47D | 116A | 116D | 48B | 46A | 46A | 116C |
| $C_9$ | 59A | 116C | 116D | 57D | 115B | 116D | 59D | 53A | 60C | 116D |
| $C_{10}$ | 95A | 115B | 114B | 94C | 115A | 114B | 95C | 201B | 97D | 114D |
| $C_{11}$ | 103A | 188A | 200C | 200C | 116B | 200C | 187D | 83B | 187C | 200C |
| $C_{12}$ | 114A | 115A | 113C | 113C | 114D | 113C | 115B | 116B | 111B | 113C |
| $C_{13}$ | 187B | 122B | 121C | 180D | 114B | 121C | 181D | 199C | 181D | 119C |
| $C_{14}$ | 187A | 120C | 120D | 60C | 114C | 120D | 58C | 201B | 58D | 119D |
| $C_{15}$ | 79A | 119B | 119C | 183C | 114A | 187B | 185C | 201C | 181D | 181D |
| $C_{16}$ | 200A | 122A | 187B | 187C | 187B | 187C | 200D | 201A | 183C | 182A |

TABLE 7

Table for correspondence of colour codes based on Flower Council of Holland.

| Codes | Group |
|---|---|
| 1–13 | Yellow group |
| 14–23 | Yellow - Orange group |
| 24–29 | Orange group |
| 30–35 | Orange - Red group |
| 36–56 | Red group |
| 57–74 | Red - Purple group |
| 75–79 | Purple group |
| 80–82 | Purple - Violet group |
| 83–88 | Violet group |
| 89–98 | Violet - Blue group |
| 99–110 | Blue group |
| 111–124 | Blue - Green group |
| 125–143 | Green group |
| 144–154 | Yellow - Green group |
| 155 | White group |
| 156–157 | Grey - White group |
| 158–159 | Orange - White group |
| 160–162 | Greyed - Yellow group |
| 163–177 | Greyed - orange group |
| 178–182 | Greyed - Red group |
| 183–187 | Greyed - Purple group |
| 188–198 | Greyed - Green group |
| 199–200 | Brown group |
| 201 | Grey group |
| 202 | Black group |

The various colours shown above are codified according to RHS colour chart in association with Flower Council of Holland and The Royal Horticultural Society, London The main advantages of the present invention are:
1. Herbal colourants offer an advantage in that they can be added or used without taking into consideration certification by different agencies like FAO, WHO and Cosmetic authorities etc.
2. The herbal colourants are safe, eco-friendly and health protective.

3. These herbal colourants may be used in more sensitive and delicate parts of the body like lips, cheeks and eyelids.
4. These herbal colourants can be used in leucoderma particularly of lips region.
5. The herbal colours are 100% lipophilic in nature.
6. The herbal colours are antimicrobial and anti-inflammatory.
7. The herbal colours are free from any strong side effects like carcinogenic effects to the users.
8. The herbal colours can be made in different shades in a cost-effective manner.
9. Addition of different essential oil and their isolates promotes the stimulation of creative thoughts, enhance sensual feeling induce positive mental health and well being and to help to overcome the depressant feelings (anti-depressant).

Thus, the of the present invention is to develop a safe and eco-friendly health protective and beauty enhancing herbal functional composition that contains only the natural products. The natural safe colour has been obtained and developed from different plant species belonging to the genus *Amebia, Bixa, Butea, Carthamus, Hibiscus, Jatropha, Lithospermum, Macrotomia, Maharanga, Nyctanthes, Onosma, Rhododendron* and *Tagetes*. Various shades of colours were differentially extracted by following certain well-defined extraction methods. The invention also seeks to use lipstick as a medium of aroma therapy. Essential oils isolated from different plants belonging to the genus *Aquilaria, Cinnamomum, Cymbopogon, Elettaria, Eucalyptus, Geranium, Jasminum, Ocimum, Pelargonium, Rosa, Rosmarinus, Santalum* and *Vetiveria* etc. Various blends of these essential oil isolates have been used to get desired effect like anti-depressant and creative thoughts.

The invention claimed is:

1. A lipstick cosmetic composition comprising:
   an herbal colorant isolated from a species belonging to the genera of the family Boraginaceae; and
   a cosmetically acceptable amount of one or more additives selected from essential oils/aroma isolates obtained from the group of plant species belonging to genera *Acquillaria, Cinnamomum, Cymbopogon Elettaria, Eucalyptus, Geranium, Jasminum, Ocimum, Pelargonium, Rosa, Rosmarinus, Santalum or Vetiveria;*
   wherein the herbal colorant and one or more additives are present in the lipstick, and
   wherein in said genera of the family Boraginaceae are selected from *Arnebia, Bixa, Butea, Carthamus, Hibiscus, Jatropha, Lithospermum, Macrotomia, Maharanga, Nyctanthes, Onosma, Rhododendrom and Tagetes,*
   the herbal colorant is extracted from root, stem or leaves of the Boraginaceae plant,
   the pH of the herbal colorant is in the range of 5.0 to 6.0,
   the composition contains 0.1 to 10 wt. % of the herbal colorant and
   the herbal colorant is soluble in an organic solvent selected from hexane, petroleum ether, benzene, diethyl ether, ethylacetate, chloroform, acetone and alcohol.

2. A lipstick composition as claimed in claim 1, wherein said composition is non-toxic.

3. A lipstick composition as claimed in claim 1, wherein the shades of the herbal colorants may be changed to different shades by treating with organic and inorganic acids.

4. A lipstick composition as claimed in claim 3, wherein the intensity of the herbal colorants may be increased by treating with organic acids or decreased by treating with inorganic acids.

5. A lipstick composition as claimed in claim 3, wherein the concentration of the acids used is in the range of 0.05 to 20% of the weight of the herbal colorants.

6. A lipstick composition as claimed in claim 1, wherein the shades of the herbal colorants may be changed by treating with organic and inorganic bases.

7. A lipstick composition as claimed in claim 6, wherein the intensity of the herbal colorants maybe increased by treating with organic bases or decreased by treating with inorganic bases.

8. A lipstick composition as claimed in claim 6, wherein the concentration of the bases used is in the range of 0.05 to 20% by weight of the herbal colorants.

9. A lipstick composition as claimed in claim 1, wherein the composition comprises essential oils/aroma isolates in the range of 1 ppm to 90 ppm.

10. A lipstick composition as claimed in claim 1, wherein the essential oils/aroma isolates used are in the range of 0.0001 to 0.009% of the total weight of the composition.

11. An eye shadow cosmetic composition comprising:
    an herbal colorant isolated from a species belonging to the genera of the family Boraginaceae; and
    a cosmetically acceptable amount of one or more additives selected from essential oils/aroma isolates obtained from the group of plant species belonging to genera *Acquillaria, Cinnamomum, Cymbopogon Elettaria, Eucalyptus, Geranium, Jasminum, Ocimum, Pelargonium, Rosa, Rosmarinus, Santalum or Vetiveria;*
    wherein the herbal colorant and one or more additives are present in the eye shadow, and
    wherein in said genera of the family Boraginaceae are selected from *Arnebia, Bixa, Butea, Carthamus, Hibiscus, Jatropha, Lithospermum, Macrotomia, Maharanga, Nyctanthes, Onosma, Rhododendrom and Tagetes,*
    the herbal colorant is extracted from root, stem or leaves of the Boraginaceae plant,
    the pH of the herbal colorant is in the range of 5.0 to 6.0,
    the composition contains 0.1 to 10 wt. % of the herbal colorant and
    the herbal colorant is soluble in an organic solvent selected from hexane, petroleum ether, benzene, diethyl ether, ethylacetate, chloroform, acetone and alcohol.

12. An eye shadow composition as claimed in claim 11, wherein the composition comprises essential oils/aroma isolates in the range of 1 ppm to 90 ppm.

13. An eye shadow composition as claimed in claim 11, wherein the essential oils/aroma isolates used are in the range of 0.0001 to 0.009% of the total weight of the composition.

14. A glitter cosmetic composition comprising:
    an herbal colorant isolated from a species belonging to the genera of the family Boraginaceae; and
    a cosmetically acceptable amount of one or more additives selected from essential oils/aroma isolates obtained from the group of plant species belonging to genera *Acquillaria, Cinnamomum, Gymbopogon Elettaria, Eucalyptus, Geranium, Jasminum, Ocimum, Pelargonium, Rosa, Rosmarinus, Santalum or Vetiveria;*
    wherein the herbal colorant and one or more additives are present in the glitter, and wherein in said genera of the family Boraginaceae are selected from *Arnebia, Bixa, Butea, Carthamus, Hibiscus, Jatropha, Lithospermum, Macrotomia, Maharanga, Nyctanthes, Onosma, Rhododendrom and Tagetes,* the herbal colorant is extracted from root, stem or leaves of the Boraginaceae plant, the pH of the herbal colorant is in the range of 5.0 to 6.0, the composition contains 0.1 to 10 wt. % of the herbal colorant and the herbal colorant is soluble in an organic solvent selected from hexane, petroleum ether, benzene, diethyl ether, ethylacetate, chloroform, acetone and alcohol.

15. A glitter composition as claimed in claim 14, wherein the composition comprises essential oils/aroma isolates in the range of 1 ppm to 90 ppm.

16. A glitter composition as claimed in claim 14, wherein the essential oils/aroma isolates used are in the range of 0.0001 to 0.009% of the total weight of the composition.

17. A rouge cosmetic composition comprising:

an herbal colorant isolated from a species belonging to the genera of the family Boraginaceae;

a cosmetically acceptable amount of one or more additives selected from essential oils/aroma isolates obtained from the group of plant species belonging to genera *Acquillaria, Cinnamomum, Cymbopogon Elettaria, Eucalyptus, Geranium, Jasminum, Ocimum, Pelargonium, Rosa, Rosmarinus, Santalum or Vetiveria;* wherein the herbal colorant and one or more additives are present in the rouge, wherein in said genera of the family Boraginaceae are selected from *Arnebia, Bixa, Butea, Carthamus, Hibiscus, Jatropha, Lithospermum, Macrotomia, Maharanga, Nyctanthes, Onosma, Rhododendrom and Tagetes,* the herbal colorant is extracted from root, stem or leaves of the Boraginaceae plant, the pH of the herbal colorant is in the range of 5.0 to 6.0, the composition contains 0.1 to 10 wt. % of the herbal colorant and the herbal colorant is soluble in an organic solvent selected from hexane, petroleum ether, benzene, diethyl ether, ethylacetate, chloroform, acetone and alcohol.

18. A rouge composition as claimed in claim 17, wherein the composition comprises essential oils/aroma isolates in the range of 1 ppm to 90 ppm.

19. A rouge composition as claimed in claim 17, wherein the essential oils/aroma isolates used are in the range of 0.0001 to 0.009% of the total weight of the composition.

* * * * *